United States Patent
Kaye et al.

(10) Patent No.: US 7,214,488 B2
(45) Date of Patent: May 8, 2007

(54) DETECTION OF MECT1-MAML2 FUSION PRODUCTS

(75) Inventors: Frederic J. Kaye, Potomac, MD (US); Giovanni Tonon, Watertown, MA (US)

(73) Assignee: United States of America, Represented by the Secretary, Department of Health and Human Services, Washington, DC (US)

( * ) Notice: Subject to any disclaimer, the term of this patent is extended or adjusted under 35 U.S.C. 154(b) by 199 days.

(21) Appl. No.: 10/479,546

(22) PCT Filed: Jul. 3, 2002

(86) PCT No.: PCT/US02/21344

§ 371 (c)(1),
(2), (4) Date: Mar. 29, 2004

(87) PCT Pub. No.: WO03/004645

PCT Pub. Date: Jan. 16, 2003

(65) Prior Publication Data

US 2004/0180349 A1 Sep. 16, 2004

Related U.S. Application Data

(60) Provisional application No. 60/302,788, filed on Jul. 3, 2001.

(51) Int. Cl.
*C12Q 1/68* (2006.01)
*C12P 19/34* (2006.01)
*G01N 33/53* (2006.01)
*G01N 33/48* (2006.01)

(52) U.S. Cl. .......................... 435/6; 435/91.2; 435/7.1; 435/40.5

(58) Field of Classification Search ...................... None
See application file for complete search history.

(56) References Cited

U.S. PATENT DOCUMENTS

| | | | |
|---|---|---|---|
| 5,567,586 A | 10/1996 | Croce | |
| 5,637,471 A | 6/1997 | Artavanis-Tsakonas et al. | |
| 5,786,158 A | 7/1998 | Artavanis-Tsakonas et al. | |
| 6,083,904 A | 7/2000 | Artavanis-Tsakonas | |
| 6,130,043 A | 10/2000 | Billing-Medel et al. | |
| 6,174,674 B1 | 1/2001 | Morris et al. | |

OTHER PUBLICATIONS

El-Naggar et al. A mucoepidermoid carcinoma of minor salivary gland with t(11;19)(q21;p13.1) as the only karyotypic abnormality. Cancer Genet Cytogenet. vol. 87, No. 1, pp. 29-33, Mar. 1996.*

Toida et al. Analysis of genetic alterations in salivary gland tumors by comparative genomic hybridization. Cancer Genet Cytogenet. vol. 127, No. 1, pp. 34-37, May 2001.*

Kirchhoff et al. High resolution comparative genomic hybridisation in clinical cytogenetics. J Med Genet. vol. 38, No. 11, pp. 740-744, Nov. 2001.*

Nordkvist et al. Cytogenetic observations in 13 cystadenolymphomas (Warthin's tumors). Cancer Genet Cytogenet. vol. 76, No. 2, pp. 129-135, Sep. 1994.*

Nordkvist et al. Recurrent rearrangements of 11q14-22 in mucoepidermoid carcinoma. Cancer Genet Cytogenet. vol. 74, No. 2, pp. 77-83, Jun. 1994.*

Behboudi et al. Molecular classification of mucoepidermoid carcinomas-Prognostic significance of the MECT-MAML2 fusion oncogene. Genes Chromosomes Cancer. vol. 45, No. 5, pp. 470-481, May 2006.*

Kroese et al. Genetic tests and their evaluation: can we answer the key questions? Genet Med. vol. 6, pp. 475-480, 2004.*

Stenman et al. A child with a t(11;19)(q14-21;p12) in a pulmonary mucoepidermoid carcinoma. Virchows Arch. vol. 433, No. 6, pp. 579-581, Dec. 1998.*

Bullerdiek et al. Translocation t(11;19)(q21;p13.1) as the sole chromosome abnormality in a cystadenolymphoma (Warthin's tumor) of the parotid gland. Cancer Genet Cytogenet. vol. 35, No. 1, pp. 129-132, Oct. 1988.*

AP000865.2, GI: 8119013, publicly available May 30, 2000.*

AC011875.3, GI: 7107950, publicly available Mar. 12, 2000.*

Nasedkina et al. Identification of chromosomal translocations in leukemias by hybridizatin with oligonucleotide microarrays. Haematologica, vol. 87, No. 4, pp. 363-372, Apr. 2002.*

Rogan et al. Sequence-based design of single-copy genomic DNA probes for fluorescence in situ hybridization. Genome Research, vol. 11, No. 6, pp. 1086-1094, Jun. 2001.* von Bergh et al. A DNA probe combination for imprived detection of MLL/11q23 breakpoints by double-color interphase-FISH in acute leukemias. Genes, Chromosomes & Cancer, vol. 28, pp. 14-22, 2000.*

(Continued)

*Primary Examiner*—Celine Qian
*Assistant Examiner*—Jennifer Dunston
(74) *Attorney, Agent, or Firm*—Leydig, Voit & Mayer, Ltd.

(57) ABSTRACT

The present invention provides methods and compositions for the diagnosis and treatment of cancer, including cancers involving the NOTCH pathway. In particular, the present invention provides methods and compositions for the diagnosis of mucoepidermoid carcinoma, the most common malignant salivary gland tumor. The present invention further provides methods and compositions for the diagnosis of other tumors associated with the t(11;19)(q14–21;12–13) translocation.

12 Claims, 9 Drawing Sheets

OTHER PUBLICATIONS

Allman et al., "An Invitation to T and More: Notch Signaling in Lymphopoiesis," *Cell*, vol. 109, pp. S1-S11 (2002).

Artavanis-Tsakonas et al., "Notch Signaling," *Science*, vol. 268, pp. 225-232.

Aster et al., "Notch Signaling in Leukemia," *Curr. Opin. Hematol.*, vol. 8, pp. 237-244 (2001).

Aster et al., "Essential Roles for Ankyrin Repeat and Transactivation Domains in Induction of T-Cell Leukemia by Notch1," *Mol. Cell. Biol.*, vol. 20 (20), pp. 7505-7515 (2000).

Calcaterra, "Salivary Glands," *Cancer Treatment*, 4th ed. (Haskell, ed.), *W.B. Saunders Company, Philadelephia*, Chapter 62, pp. 721-726 (1995).

Carney et al., "Establishment and Identification of Small Cell Lung Cancer Cell Lines Having Classic and Variant Features," *Cancer Res.*, vol. 45, pp. 2913-2923 (1985).

Dahlenfors et al., "Translocation(11:19)(q14-21;P12) in a Parotid Mucoepidermoid Carcinoma of a Child," *Cancer Genet. Cytogenet.*, vol. 79, p. 188 (1995).

Dahlenfors et al., "A Fourth Minor Salivary Gland Mucoepidermoid Carcinoma with 11q14-21 and 19p12 Rearrangements," *Hereditas*, vol. 120, pp. 287-288 (1994).

GenBank Assession No. AB014516, May 26, 1998.
GenBank Accession No. AB058772, Mar. 27, 2001.
GenBank Accession No. AE003523, Mar. 21, 2000.
GenBank Accession No. AF221759, Jan. 6, 2000.
GenBank Accession No. AK024089, Aug. 23, 2000.
GenBank Accession No. AY040322, Jun. 14, 2001.
GenBank Accession No. BAA31591, May 26, 1998.
GenBank Accession No. BAB47448, Mar. 27, 2001.
GenBank Accession No. NM_025021, (2003).
GenBank Accession No. NT_008984, (2003).
GenBank Accession No. X54251, Aug. 8, 1990.
GenBank Accession No. XM_011324, May 9, 2002.
GenBank Accession No. XM_045716, (2003).
GenBank Accession No. XM_059064, Feb. 6, 2002.

Horsman et al., "Translocation (11:19)(q21;p13.1) in Mucoepidermoid Carcinoma of Salivary Gland," *Cancer Genet. Cytogenet.*, vol. 80, pp. 165-166 (1995).

Hsieh et al., "Truncated Mammalian Notch1 Activated CBF1/RBPJk-Repressed Genes by a Mechanism Resembling That of Epstein-Barr virus EBNA2," *Mol. Cell. Biol.*, vol. 16 (3), pp. 952-959 (1996).

Jin et al., "Characterization of Chromosome Aberrations in Salivary Gland Tumors by FISH, Including Multicolor COBRA-FISH," *Genes Chromosomes Cancer*, vol. 30, pp. 161-167 (2001).

Johansson et al., "Translocation 11;19 in a Mucoepidermoid Tumor of the Lung," *Cancer Genet. Cytogenet.*, vol. 80, pp. 85-86 (1995).

Kas et al., "Promoter Swapping Between the Genes for a Novel Zinc Finger Protein and β-catenin in Pleiomorphic Adenomas with t(3;8)(p21;q12) Translocations," *Nat. Genet.*, vol. 15, pp. 170-174 (1997).

Kojika et al., "Notch Receptors and Hematopoiesis," *Exp. Hematol.*, vol. 29, pp. 1041-1052 (2001).

Martins et al., "Cytogenic Characterisation of Warthin's Tumour," *Oral Oncol.*, vol. 33 (5), pp. 344-347 (1997).

Martins et al., "Malignant Salivary Gland Neoplasms: a Cytogenetic Study of 19 Cases," *Oral Oncol., Eur. J. Cancer*, vol. 32B (2), pp. 128-132 (1996).

Mitelman, "Recurrent Chromosome Aberrations in Cancer," *Mutat. Res.*, vol. 462, pp. 247-253 (2000).

Modi et al., "Protein Expression of the RB-related Gene Family and SV40 Large T Antigen in Mesothelioma and Lung Cancer," *Oncogene*, vol. 19, pp. 4632-4639 (2000).

Petcherski et al., "Mastermind is a Putative Activator for Notch," *Curr. Biol.*, vol. 10 (13), pp. R471-R473 (2000).

Petcherski et al., "LAG-3 is a Putative Transcriptional Activator in the *C. elegans* Notch Pathway," *Nature*, vol. 405, pp. 364-368 (2000).

Schoenmakers et al., "Recurrent Rearrangements in the High Mobility Group Protein Gene, *HMGI-C*, in Benign Mesenchymal Tumours," *Nat. Genet.*, vol. 10, pp. 436-444 (1995).

Tonon et al., "Spectral Karyotyping Combined with Locus-Specific FISH Simultaneously Defines Genes and Chromosomes involved in Chromosomal Translocations," *Genes Chromosomes Cancer*, vol. 27, pp. 418-423 (2000).

Vokes et al., "Head and Neck Cancer," *New Eng. J. Med.*, vol. 328 (3), pp. 184-194 (1993).

Wu et al., "MAML1, a Human Homologue of *Drosophila* Mastermind, is a Transcriptional Co-Activator for NOTCH Receptors," *Nat Genet.*, vol. 26, pp. 484-489 (2000).

Xu et al., "The *Notch* Locus and the Genetic Circuitry Involved in Early *Drosophila* Neurogenesis," *Genes Dev.*, vol. 4, pp. 464-475 (1990).

Kaye et al., "Emerging Biology of Malignant Salivary Gland Tumors Offers New Insights into the Classification and Treatment of Mucoepidermoid Cancer," *Clin Cancer Res*. vol. 12 (13), pp. 3878-3881 (2006).

Martins et al., "A Study of MECT1-MAML2 in Mucoepidermoid Carcinoma and Warthin's Tumor of Salivary Glands," *Journal of Molecular Diagnostics*, vol. 6 (3), pp. 205-210 (2004).

Okabe et al., "MECT1-MAML2 Fusion Transcript Defines a Favorable Subset of Mucoepidermoid Carcinoma," *Clin Cancer Res*, vol. 12 (13), pp. 3902-3907 (2006).

GenBank Accession No. AB058719, Mar. 27, 2001.

* cited by examiner

A

B

| | | |
|---|---|---|
| MAML2 | YERGRAESSDRERESTLQLLSLVQHGQGARK | 58- 89 |
| MAML1 | YEAVSPERLELERQHTFALHQRCIQAKAKRA | 41- 72 |
| KIAA1819 | YQQAQVEQLELERRDTVSLYQRTLEQRAKKS | 124-155 |
| MAM | YEQAFNIVCEQNQETTVLQKRFLESKNKRA | 53-184 |
| LAG-3A | YEKARPEMIANQRAVTAHLFNRYTEDEERKR | 81-112 |

A

B

DETECTION OF MECT1-MAML2 FUSION PRODUCTS

This application claims priority to U.S. Provisional Application Ser. No. 60/302,788 filed on Jul. 3, 2001, which is herein incorporated by reference in its entirety. This invention was made in part during work supported by Federal funds from the National Cancer Institute, and as such the government has certain rights in the invention.

FIELD OF THE INVENTION

The present invention provides methods and compositions for the diagnosis and treatment of cancer, including cancers involving the NOTCH pathway. In particular, the present invention provides methods and compositions for the diagnosis of mucoepidermoid carcinoma, the most common malignant salivary gland tumor. The present invention further provides methods and compositions for the diagnosis of other tumors associated with the t(11;19)(q14–21; p12–13) translocation.

BACKGROUND OF THE INVENTION

The annual U.S. incidence rate of head and neck cancer is approximately 40,000 cases (Vokes et al., New Eng. J. Med., 328:184 [1993]). Although salivary gland tumors differ in their etiology, histology and standard therapy from most head and neck cancer, these cancers represent a significant threat to human health. Salivary gland tumors arise from either one of the three major salivary glands or from the minor salivary glands that line the mucosa of the upper aerodigestive tract. Histologically, these tumors are very heterogeneous, and include mucoepidermoid cancers, pleomorphic adenoma, and adenoid cystic carcinomas as the more frequent observed tumor types. Treatment of these tumors is predominantly surgical, with post-operative radiotherapy being frequently administered. For unresectable tumors, neutron irradiation has been used in place of conventional radiotherapy. Chemotherapy is typically reserved for patients with recurrent or metastatic disease.

Mucoepidermoid carcinoma (MEC) is the most common malignant human salivary gland tumor which can arise from both major (parotid) and minor salivary glands, including serous/mucous glands within the pulmonary tracheobronchial tree (Calcaterra, in *Cancer Treatment*, 4$^{th}$ ed. (Haskell, ed.), W. B. Saunders Company, Philadelphia, [1995], at pages 721–726). These salivary gland tumors may be deadly, due to their tendency to grow locally and recur aggressively, if not completely excised. However, complete excision is difficult due to the three-dimensional growth pattern of these tumors, which make it difficult for the surgeon to accurately determine when clean margins have been achieved. Pathologic analysis using light microscopy is currently employed to assess tumor margins and to help determine the need for post-operative radiotherapy. However, this approach does not necessarily provide sufficient sensitivity for optimal patient management. In addition, both surgeons and patients desire minimal surgical approaches for cosmetic reasons, as well as to preserve nerve function to the facial area. Thus, methods and compositions suitable for the rapid and reliable diagnosis of these and other aggressive tumors are needed.

SUMMARY OF THE INVENTION

The present invention provides methods and compositions for the diagnosis and treatment of cancer, including cancers involving the NOTCH pathway. In particular, the present invention provides methods and compositions for the diagnosis of mucoepidermoid carcinoma, the most common malignant salivary gland tumor. The present invention further provides methods and compositions for the diagnosis of other tumors associated with the t(11;19)(q14–21; p12–13) translocation.

The present invention provides compositions and methods to definitively diagnose mucoepidermoid carcinomas and other tumors that are associated with the t(11;19) (q14–21; p12–13) translocation. In some embodiments, the present invention provides diagnostic means that utilize minimal biopsy samples. In particularly preferred embodiments, the present invention provides methods and compositions suitable for testing of fine needle aspirate samples. In some additional preferred embodiments, the present invention provides methods and compositions for FISH analysis of tumor cells, while in alternative embodiments, the present invention provides methods and compositions for RT-PCR analysis of RNA extracted from tumor cells.

The present invention also provides BAC clones useful for consistent markers of the translocation of interest. In particularly preferred embodiments, the two adjacent BAC clones from human chromosome 11q21, designated as "RP11-676L3" and "RP11-16K5" are used as consistent markers for the translocation. RP11-676L3 contains exon 1 of the MAML2 gene and is retained on the derivative 11 chromosome, while RP11-16K5 contains exons 2–5 of the MAML2 gene and is translocated to the derivative 19 chromosome. FISH hybridization with these BAC probes provides means to detect normal chromosome 11 and provides evidence for the t(11;19) translocation.

The present invention also provides methods and compositions for RT-PCR analysis using gene-specific oligonucleotides. In some embodiments, the present invention provides means to detect specific MECT1/MAML2 fusion products in biopsy samples. These embodiments of the present invention provide much greater sensitivity than the conventional light microscopy methods that are presently routinely used. In preferred embodiments, these methods and compositions provide means to obtain data within 24 hours. In particularly preferred embodiments, with optimization of reagents and test system parameters, the testing analysis is completed within 6 to 7 hours.

The present invention also provides methods and compositions for improvement of pre- and/or post-operative management of patients with mucoepidermoid carcinomas and other tumors associated with the t(11;19) translocation. In some embodiments, the present invention provides means for three-dimensional mapping of the precise location of residual tumor material. In particularly preferred embodiments, the present invention provides means to map irregular tumor margins in three dimensions, either intraoperatively and/or post-operatively. Thus, the molecular mapping of tumor margin methods and compositions of the present invention facilitate treatment regimens, as the data obtained using the present invention help the surgeon and patient determine whether repeat resection is required, and/or whether post-operative radiation therapy is necessary and/or desirable. In some embodiments, FISH analysis is utilized, while in other embodiments, RT-PCR is utilized.

The present invention further provides methods and compositions to analyze disruptions in the NOTCH signal transduction pathway. In particularly preferred embodiments, tumors carrying the t(11;19) translocation are identified as having disruptions in the NOTCH signal transduction pathway. In some embodiments, the aspects of the NOTCH pathway associated with differentiation of central nervous system and hematopoietic tissues, as well as the genesis of epithelial carcinomas are involved. In some embodiments, the present invention provides means to identify the mutant fusion product MECT1/Mastermind-like 2, which retains the transactivation domain for the NOTCH/Mastermind complex, but lacks the amino-terminal binding site for the NOTCH product. In alternative embodiments, the present invention provides means to analyze inhibitors of the transactivation domain of MAML2 for their ability to act as potential targets for the treatment of mucoepidermoid carcinomas and other tumors associated with NOTCH gene deregulation. In some embodiments, the inhibitors are small molecules. In alternative embodiments, the inhibitors are monoclonal or polyclonal antibodies.

The present invention provides methods of screening a tissue sample from a subject for a t(11;19)(q14–21; p12–13) translocation, comprising detecting the presence of a MECT1-MAML2 chimeric nucleic acid in a tissue sample. In some embodiments, the tissue sample comprises biopsy material. In preferred embodiments, the biopsy material comprises cells from a salivary gland tumor. In related embodiments, the salivary gland tumor is selected from the group consisting of a mucoepidermoid cancer, a pleomorphic adenoma, and a adenoid cystic carcinoma. In some embodiments, the MECT1-MAML2 chimeric nucleic acid comprises DNA. In related embodiments, the detecting is by fluorescence in situ hybridization, by amplifying at least a portion of said MECT1-MAML2 DNA by polymerase chain reaction, or by Southern blot. In other embodiments, the MECT1-MAML2 chimeric nucleic acid comprises RNA. In related embodiments, the detecting is by amplifying at least a portion of a MECT1-MAML2 mRNA by reverse-transcriptase polymerase chain reaction, by Northern blot, or by microarray.

The present invention also provides methods of screening a tissue sample from a subject for a t(11;19)(q14–21; p12–13) translocation, comprising detecting the presence of a MECT1-MAML2 chimeric protein in a tissue sample. In related embodiments, the detecting is by immunoblot, or by immunofluorescence analysis.

In other embodiments, the present invention provides kits for screening a tissue sample from a subject for a t(11;19)(q14–21; p12–13) translocation, comprising: a reagent capable of specifically detecting the presence of a MECT1-MAML2 chimeric nucleic acid in a tissue sample; and instructions for using the kit for screening a tissue sample from a subject for a t(11;19)(q14–21; p12–13) translocation. In some embodiments, the reagent comprises a first nucleic acid probe complementary to at least a portion of MECT1 exons 2–18, and a second nucleic acid probe complementary to at least a portion of MAML2 exon 1. In other embodiments, the reagent comprises a first nucleic acid probe complementary to at least a portion of MECT1 exon 1, and a second nucleic acid probe complementary to at least a portion of MAML2 exons 2–5. In related embodiments, the reagent comprises a first bacterial artificial chromosome designated as RP11-676L3, and a second bacterial artificial chromosome designated as RP11-16K5. In some embodiments, the first nucleic acid probe comprises a sense oligonucleotide, and the second nucleic acid probe comprises an antisense oligonucleotide.

The present invention also provides methods of screening compounds, comprising: providing: a cell containing a MECT1-MAML1 chimeric gene; and at least one test compound; and contacting the cell with the test compound; and detecting a change in MECT1-MAML2 expression in the cell in the presence of the test compound relative to the absence of the test compound. In some embodiments, the cell is selected from the group consisting of a cell transfected with a MECT1-MAML2 expression vector, and a cell with a t(11;19)(q14–21; p12–13) translocation. In other embodiments, the cell is selected from the group consisting of a cell in vitro and a cell in vivo. In some embodiments, the detecting comprises detecting MECT1-MAML2 mRNA or detecting MECT1-MAML2 protein.

DESCRIPTION OF THE FIGURES

FIG. 1, Panel B shows the results of an RT-PCR analysis using MECT1 exon 1 (sense) and MAML2 exon 2 (antisense) oligonucleotides as indicated. Lanes 1, 8, and 9 correspond to size markers, lanes 2 and 10 correspond to negative control reactions, lanes 3–5 and 11–13 correspond to reactions performed with RNA derived from MEC tumors and lanes 6 and 7 correspond to reactions performed with RNA derived from non-MEC tumors.

DESCRIPTION OF THE INVENTION

Figure 1:
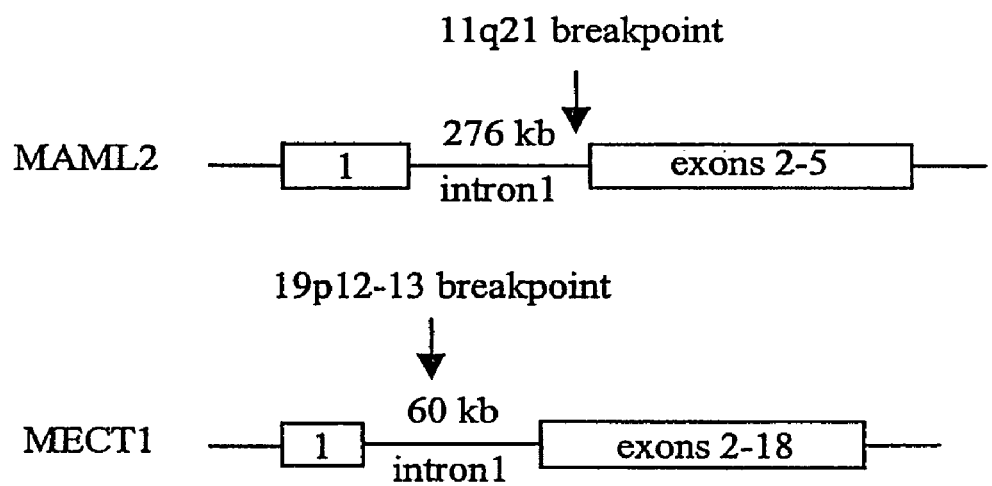
FIG. 1, Panel A provides a schematic representation of the partial genomic structure of the MAML2 and MECT1 genes and the approximate location of the translocation breakpoint.
Figure 1:
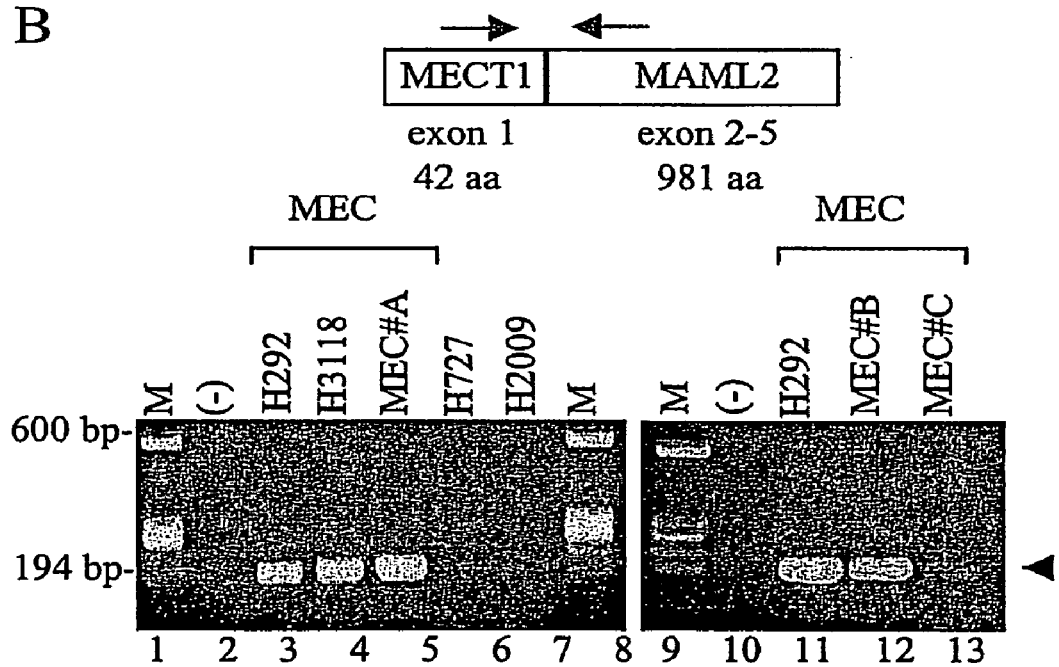

The present invention provides methods and compositions for the diagnosis and treatment of cancer, including cancers involving the NOTCH pathway. In particular, the present invention provides methods and compositions for the diagnosis of mucoepidermoid carcinoma, the most common malignant salivary gland tumor. The present invention further provides methods and compositions for the diagnosis of other tumors associated with the t(11;19)(q14–21; p12–13) translocation.

As indicated above, mucoepidermoid carcinoma (MEC) is the most common malignant human salivary gland tumor which can arise from both major (parotid) and minor salivary glands, including serous/mucous glands within the pulmonary tracheobronchial tree. Recently, cytogenetic studies have demonstrated a t(11;19)(q14–21; p12–13) translocation in 12 patients with MEC obtained from different tissue sites. In five of these cases, the t(11;19) was the sole chromosomal alteration (Johansson, et al., Cancer Genet. Cytogenet., 80:85–86 [1995]; Horsman et al., Cancer Genet. Cytogenet., 80:165–166 [1995]; El-Naggar et al., Cancer Genet. Cytogenet., 87:29–33 [1996]; Dahlenfors et al., Cancer Genet. Cytogenet., 79:188 [1995]; and Dahlenfors et al., Hereditas 120:287–288 [1994]). In addition, the same translocation event has been detected in four patients with Warthin's tumor, a distinct histologic type of parotid salivary gland tumor; in one case, it was the sole chromosomal abnormality (Bullerdiek et al., Cancer Genet. Cytogenet., 35:129–32 [1988]; Nordkvist et al., Cancer Genet. Cytogenet., 76:129–135 [1994]; and Martins et al., Oral Oncol., 33: 344–347 [1997]).

As discussed in greater detail below, by providing the identification of a tumor-specific, mutant MECT1/MAML2 fusion protein, the present invention provides methods and compositions applicable to cell biology, genetics, and diagnosis of this important class of human salivary/mucous gland tumors. While the classification of human salivary gland tumors has historically relied on histopathology by light microscopy, the distinction between benign and malignant tumors of different subtypes is often difficult, at least partially due to the presence of mixed epithelial cell types in these tumors (See, Calcaterra, supra) and to the common use of fine needle aspiration for clinical diagnosis. Pleomorphic adenoma (or benign mixed tumor) is the most common benign tumor arising from the parotid and other upper aerodigestive tract glands and has been recently associated with chromosomal rearrangements at 8q12 or 12q13–15 that activate the PLAG1 and/or HMGIC gene families, respectively (Kas et al., Nat. Genet., 15:170–174 [1997]; and Schoenmakers et al., Nat. Genet., 10:436–444 [1995]). In contrast, MEC tumors and Warthin's tumor are the most common malignant tumors arising from the parotid gland, as well as from minor serous/mucous glands scattered throughout the upper aerodigestive tract.

During the development of the present invention, it was determined that these tumors with a t(11;19)(q14–21; p12–13) are characterized by the expression of a unique chimeric MECT1/MAML2 product which may be pathogenic for these specific tumors. Finally, adenoid cystic carcinomas are the second most common type of malignant salivary gland tumor and are associated with several different chromosomal alterations including the detection of a del(6q) and t(6;9)(q21–24; p13–23), but do not demonstrate the t(11;19) rearrangement present in MEC samples (Jin et al., Genes Chromosomes Cancer 30:161–17 [2001]). Thus, the present invention provides means for a new framework for the molecular diagnosis of human MEC and Warthin's tumors, as well as providing means for pre- and/or post-surgical mapping of tumor margins to improve local control and to help the medical practitioner decide whether there is a need for adjuvant therapies. In addition, the present invention provides a means to facilitate the determination of whether these mixed lineage tumors arise from ductal epithelial stem cells or from specific committed epithelial cells, and thereby provides a new approach for understanding the biological basis for these often locally recurrent tumors.

During the development of the present invention, spectral karyotyping was performed on two independent pulmonary MEC tumor cell lines, namely NCI-H292 and H3 118. Evidence for reciprocal t(11;19) translocation was observed in both cases. Using multiple bacterial artificial chromosome (BAC) probes located at chromosome 11q14–21 for fluorescence in situ hybridization (FISH) analysis, it was determined that the immediately adjacent BAC clones, RP11-676L3 and RP11-16K5, mapped together near band q21 on the normal chromosome 11. In contrast, RP11-676L3 hybridized to the Der. chromosome 11, while RP11-16K5 mapped to the Der. 19 chromosome in both pulmonary MEC tumor cell lines. In addition, a very faint, but specific, signal from BAC RP11-676L3 was also detected on the Der. 19 chromosome indicating that the translocation breakpoint was located close to the telomeric end of RP11-676L3. Inspection of the genomic sequence in this region within chromosome 11q21 identified an open reading frame approximately 20 kb from the telomeric end of RP 11-676L3, which was contained within an anonymous mRNA sequence (designated "KIAA1819"). Protein blast search analysis (Altschul et al., J. Mol. Biol., 215:403–410 [1990]; and Altschul et al., Nucleic Acids Res., 25:3389–3402 [1997]) demonstrated that this gene shared similarity with *Drosophila* Mastermind (MAM), and with a recently identified Mastemind-like1 (MAML1) gene on human chromosome 5 that encodes a transcriptional co-activator for NOTCH receptors (Artavanis-Tsakonas et at., Science 268:225–232 [1995]; Xu et al., Genes Dev., 4, 464–475 [1990]; and Wu et al., Nat. Genet., 26:484–489 [2000]). Accordingly, this related novel gene was designated as MAML2.

Genomic blast search analyses revealed that the novel MAML2 gene (i.e., SEQ ID NO: 3) contains 5 exons and spans 340 kb at human 11q21. In addition, it was observed that the MAML2 exon 1 was contained within the BAC RP 11-16K5 (which mapped to the Der 19), while exon 2 was separated by a 270 kb intron 1, confirming that MAML2 was disrupted by a chromosomal breakpoint near the 3' end of the large MAML2 intron 1 (See, FIG. 1, Panel A). 5' rapid amplification of cDNA ends (RACE), using RNA extracted from both MEC samples revealed a single amplified product using first-strand cDNA primed independently from either the polyA tail or from a specific MAML2 exon 2 sequence. Direct nucleotide sequencing, demonstrated a chimeric mRNA species representing exon 1 of a novel gene at 19p12–3 (MECT1) fused in-frame to MAML2 exons 2–5 (See, FIG. 1, Panel B).

To confirm the expression of the MECT1-MAML2 chimeric product, RT-PCR was done using gene-specific primer pairs from MECT1 exon 1 and MAML2 exon2 with tumor RNA isolated from five different tumors: three primary tumor biopsy samples from patients with either bronchopulmonary, lingual, or parotid MEC (MEC A-C) and two cultured tumor cell lines (H292 and H3118). The identical 203 bp mutant chimera was detected in all five MEC samples (See, FIG. 1, Panel B), but not in 20 different non-MEC tumors. Additionally, by using different oligonucleotide primers, the full-length 3.7 kb MECT1/MAML2 fusion species was also detected in the MEC samples. Since MEC-C gave a relatively weak signal using the semi-quantitative RT-PCR technique, a RNase protection assay was done, confirming the presence of steady state levels of the MECT1-MAML2 chimera in MEC-B and MEC-C. Taken together, these observations indicate that the MECT1/MAML2 chimeric protein is a molecular marker for MEC tumors.

Using multiple different primer sets for MAML2 and MECT1, expression of the hypothetical, reciprocal chimeric product encoding MAML2 exon 1/MECT1 exons 2–18 was not observed. This is consistent with the expression of normal MECT1 mRNA, but not MAML2 in the MEC cell lines. An explanation for the lack of this reciprocal product includes the possibility that the MAML2 promoter is inactive in salivary and serous/mucous gland tissues, as well as the observation that this chimeric intron 1 would span approximately 300 kb which may be beyond the limits for proper splicing of a non-native intron sequence. However, an understanding of the mechanism(s) is not necessary in order to make and use the present invention.

Figure 2:
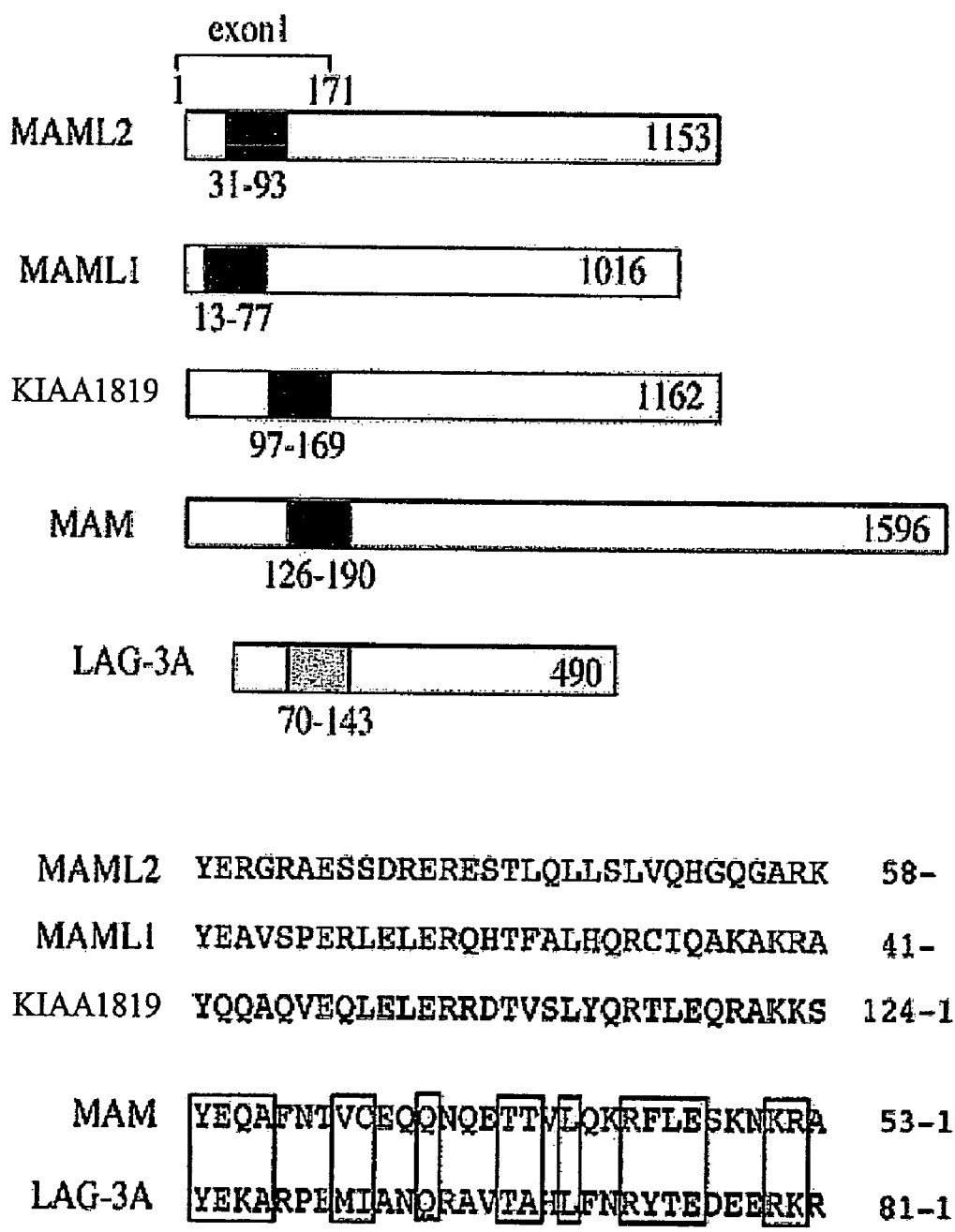
FIG. 2 provides a schema depicting the growing Mastermind-like gene family and a minimal hypothetical sequence motif. A conserved amino-terminal, highly basic domain within MAML2 (GenBank: AY040322), MAML1 (GenBank: XM 011324), an anonymous sequence, KIAA1819 (GenBank: AB058719), and Mastermind (MAM; GenBank: X54251) is indicated by a black rectangle, while an amino-terminal basic domain within the C. elegans LAG-3A gene product is depicted with a hatched rectangle. The minimal, hypothetical consensus sequences within the NOTCH binding region is shown and provided as: MAML2, SEQ ID NO: 5; MAML1, SEQ ID NO: 6; KIAA1819, SEQ ID NO: 7; MAM, SEQ ID NO: 8; and LAG-3A, SEQ ID NO: 9. Identical and conserved amino acid residues of MAM and LAG-3A are boxed.

Inspection of the MECT1 gene (i.e., SEQ ID NO: 4) at 19p12–13 showed that it contains 18 exons and has a duplicated gene sequence at chromosome 2p16.2 which is contemplated as being a pseudogene. The translated MECT1 protein sequence (i.e., SEQ ID NO: 2) has no previously defined functional motifs and shows amino acid similarities within discrete domains to only two other anonymous transcripts in the NCBI database. In contrast, the predicted sequence of MAML2 (i.e., SEQ ID NO: 1) showed 22% identity and 34% similarity over 1189 residues with the Mastermind-like homolog, MAML1. *Drosophila* Mastermind (MAM) is one of the original "neurogenic" genes, and has been identified as a component of the NOTCH signaling pathway. In particular, exon 1 of MAML2 is predicted to encode the complete conserved 'basic region' found near the amino-terminus of MAM and MAMLJ (See, FIG. 2). This charged domain has been shown to bind to the ankyrin repeats of the intracellular NOTCH receptor domain (ICN) (See e.g., Artavanis-Tsakonas et al., Science 268:225–232 [1995]; Wu et al., Nat. Genet., 26:484–489 [2000]; Aster et al., Mol. Cell. Biol., 20:7505–75 15 [2000]; and Petcherski and Kimble, Nature 405:364–8 [2000]). In addition, Psi-Blast protein alignment (Altschul et al., Nucleic Acids Res., 25:3389–402 [1997]) showed a potential, minimal NOTCH binding domain within MAML2, that is also present within an amino-terminal region of the LAG-3 gene product (Petcherski and Kimble, Nature 405:364–368 [2000]). This hypothetical alignment with Lag-3, however, lacks statistical significance and remains to be confirmed by protein binding assays.

The mammalian MAML1 has been shown to function as a transcriptional co-activator for Notch, forming a complex in the nucleus with the intracellular domain of an activated Notch receptor (ICN) and the bifunctional transcription factor CBF1/Su(h)/Lag1 (CSL; Wu et al., supra [2000]). Formation of the ICN/CSL/MAML1 complex activates the transcription of Notch target genes, including HES1, the best characterized member of the HES family (mammalian homologues of *Drosophila* Hairy and Enhancer of Split genes; Artavanis-Tsakonas et al., supra [1995]; and Kojika and Griffin, Exp. Hematol., 29:1041–1052 [2001]).

Interestingly, the ectopic expression of an in vitro MAML1 mutant gene, lacking the amino-terminal NOTCH binding domain, but retaining the carboxy-terminal transactivation domain (TAD), was recently shown to exhibit a dominant-negative phenotype by inhibiting the ability of ICN to activate its normal downstream target, the HES1 promoter (Wu et al., supra [2000]). During the development of the present invention, it was demonstrated that the t(11; 19)(q14–21; p12–13) alteration found in the most common type of malignant salivary gland tumors results in the in vivo expression of a fusion product that would also selectively lack the amino-terminal NOTCH binding domain, but retain the TAD and glutamine-rich domains that are conserved in the Mastermind-like and Lag-3 gene family.

Figure 3:
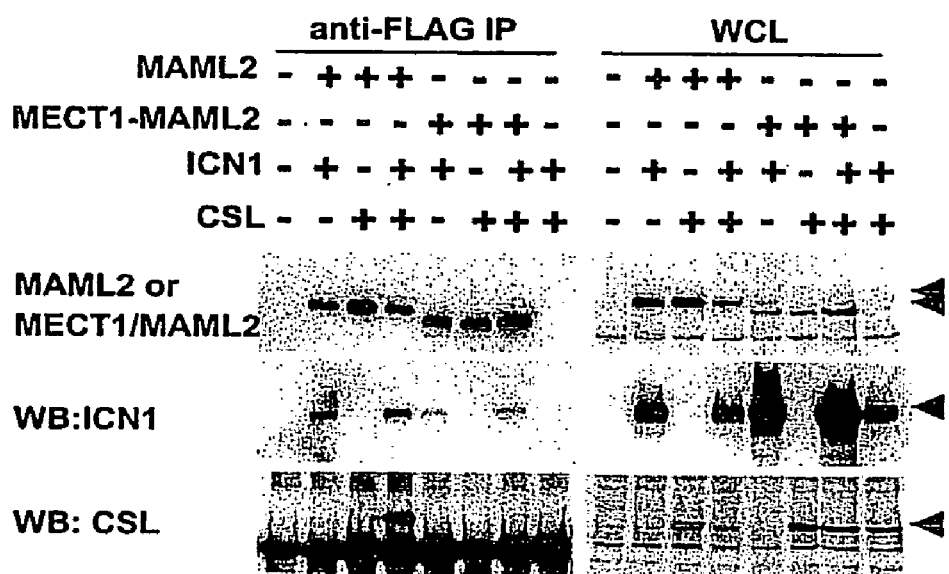
FIG. 3 shows the results of biochemical analyses of MECT1-MAML2. In Panel A, COS7 cells were co-transfected with different combinations of FLAG-tagged MAML2, FLAG-tagged MECT1-MAML2, HA-tagged ICN1, and Myc-tagged CSL as indicated. Anti-FLAG immunoprecipitates (liP) or whole cell lysates (WCL) were immunoblotted (WB) with anti-FLAG, anti-HA, or anti-myc antibodies. In Panel B, U20S cells were transfected with 0.5 µg pG5uc (containing four GAL4 binding sites and a firefly luciferase reporter), 25 ng pRL-TK plasmid encoding Renilla luciferase and 0.5 µg of GAL4 DNA binding domain (BD) only, or BD fused to MECT1-MAML2, MAML2, or MAML2 (174-1153). Activity was normalized to Renilla luciferase.
Figure 3:
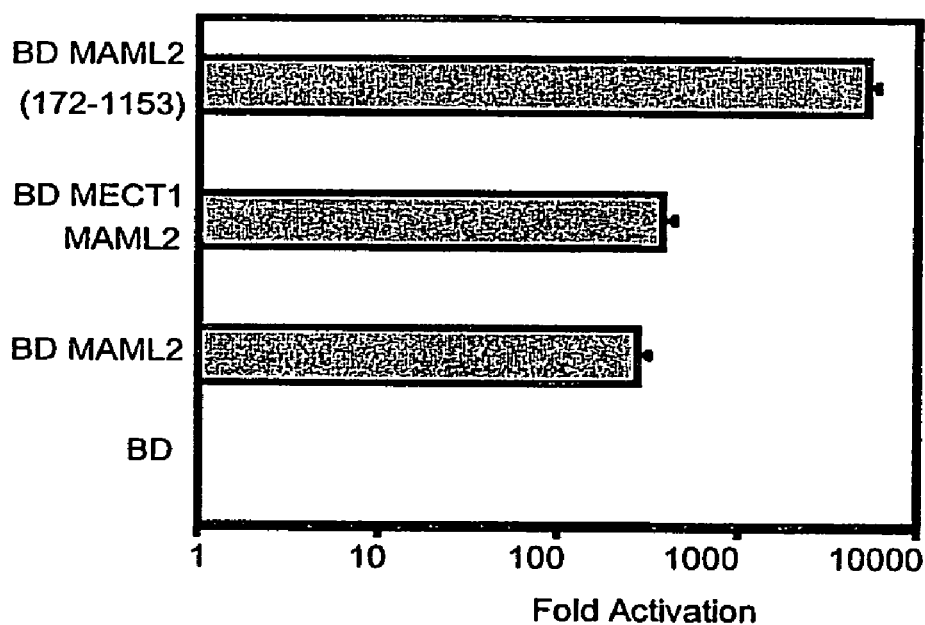

To test the function of MECT1-MAML2 and MAML2 in Notch signaling, the subcellular localization of these proteins was compared. Using a green fluorescent protein (GFP) tag or fluorescent anti-FLAG, both proteins were observed to co-localize in a nuclear structure with a speckled staining pattern, identical to that previously described for MAML1 (Wu et al., supra [2000]). Transfected ICN1-GFP localized to the nucleus in a diffuse pattern. However, coexpression of either MECT1-MAML2 or MAML2, was able to induce re-localization of ICN1 from a diffuse nuclear pattern into a distinct, speckled nuclear structure. In addition, both MECT1-MAML2 and MAML2 co-localized with ICN1 in these nuclear bodies. Immunoprecipitation was performed to determine whether MECT/MAML2 physically interacted with ICN1. As shown in FIG. 3, Panel A, both MAML2 and MECT1-MAML2 co-immunoprecipitated with ICN1, although the MECT1-MAML2 interaction with ICN appeared to be weaker. However, only MAML2 and not MECT1-MAML2, co-immunoprecipitated in a multiprotein complex with CSL and ICN1.

A transcriptional activation domain (TAD) was previously mapped to the carboterminal region of MAML1 (Wu et al., supra [2000]). To determine whether MAML2 and MECT1-MAML2 also contain a TAD, the appropriate eDNAs were fused with the Gal4 DNA binding domain (BD). As shown in FIG. 3, Panel B, both MAML2 and MECT1-MAML2 encode a functional TAD. In addition, the carboxy-terminal component of the MAML2 (exons 2–5; aa172-1153) also was observed to retain a high level of TAD activity (See, FIG. 3, Panel B).

Figure 4:
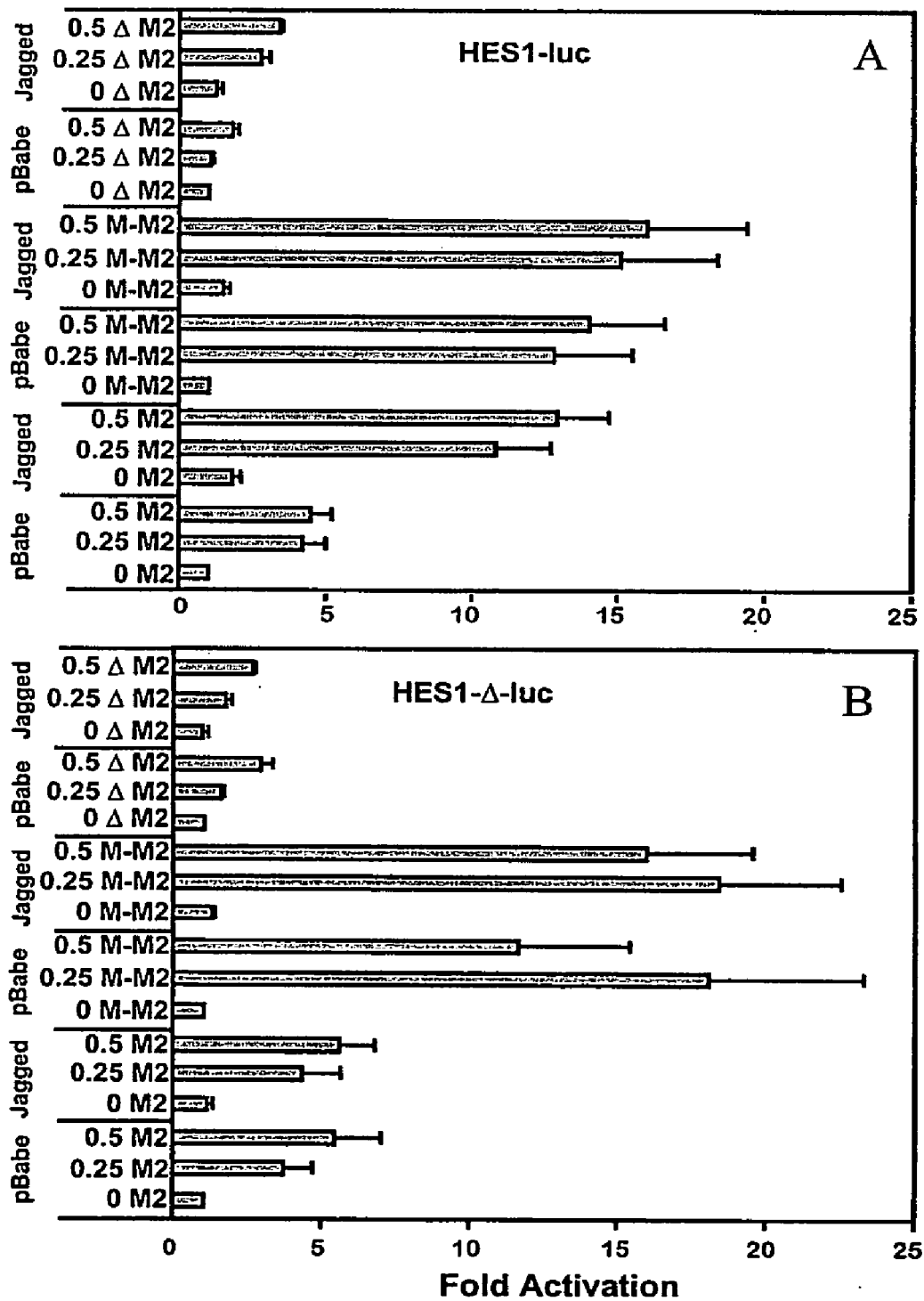
FIG. 4 indicates that MECT1-MAML2 activation is independent of Jagged2 stimulation and CSL binding sites. In Panel A, U20S cells were co-transfected with 0.5 µg of the HES1-1uc promoter construct, 25 ng pRL-TK plasmid encoding Renilla luciferase, and increasing amounts of pFLAG-CMV2 plasmids (in µg) encoding MAML2 (M2), MECTi-MAML2 (M-M2), and MAML2 (172-1153) (ΔM2). 20 h post-transfection, $10^5$ NIH 3T3 cells expressing Jagged2 or NIH 3T3 cells infected with empty pBABE virus were added to each well and luciferase activity was measured 24 h later. Panel B, shows the results of the same experimental design applied to an HES 1 promoter lacking two CSL binding sites (HES1-Δ).
Figure 5:
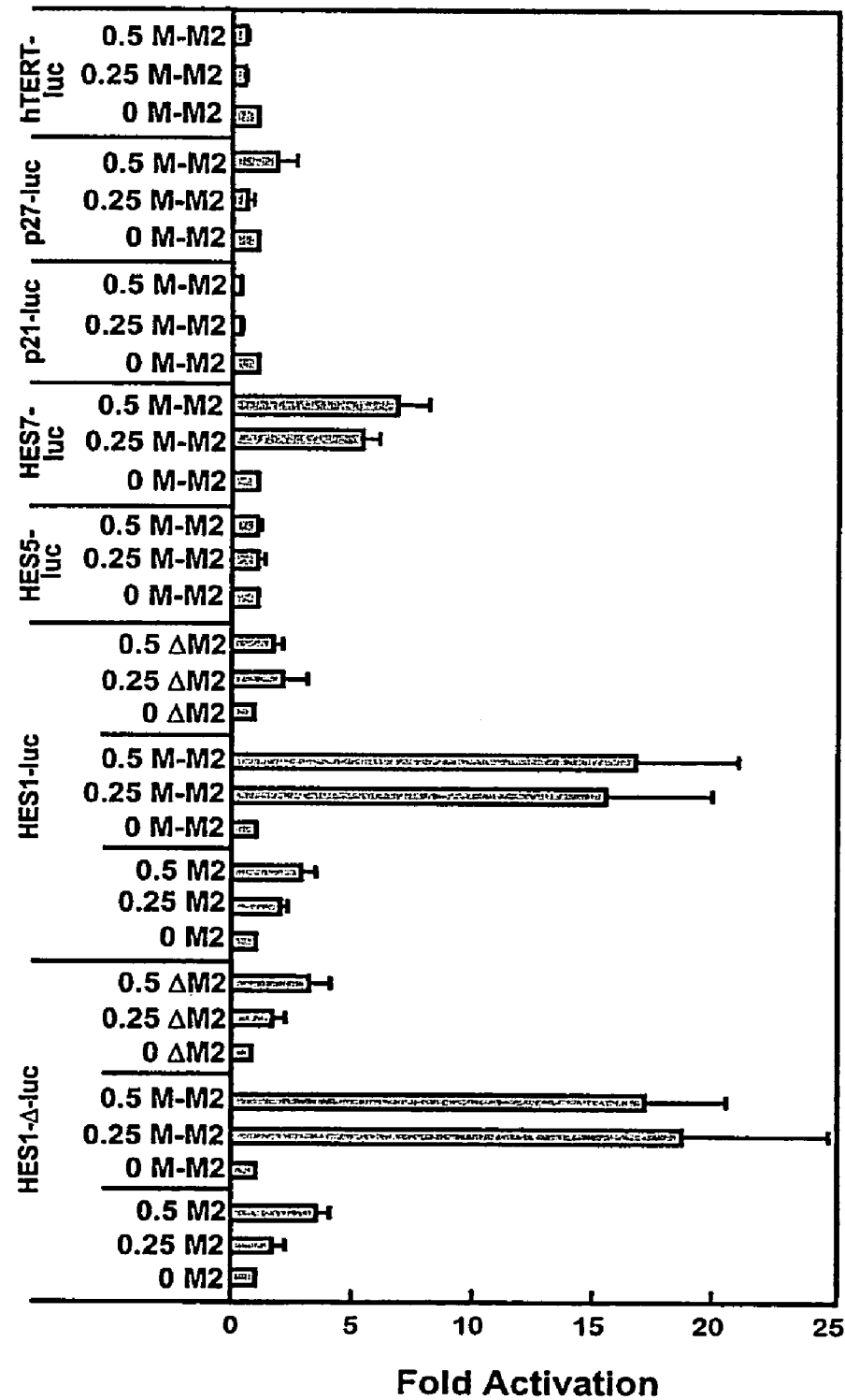
FIG. 5 indicates that MECT1-MAML2 activation shows narrow promoter specificity. U2OS cells were transfected with 0.5 μg of the indicated promoter/reporter constructs, 25 ng pRL-TK plasmid encoding *Renilla* luciferase, and increasing amounts of the indicated MECT1 -MAML2 plasmids.
Figure 6:
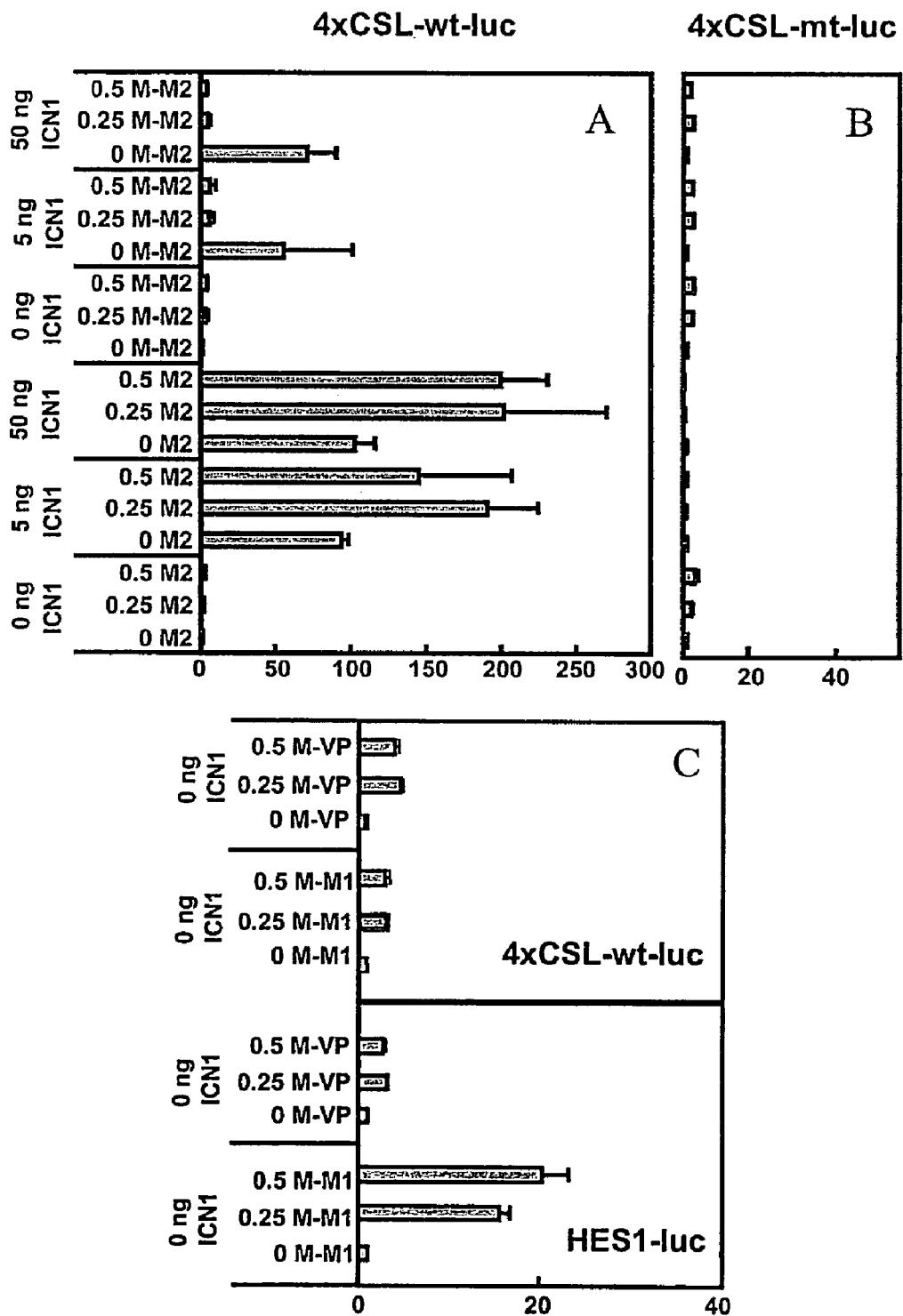
FIG. 6 indicates that MECT1 -MAML2 and MECT1 - MAML1, but not MECT1-VP16, mediates CSL-independent and ICN-independent activation. Panel A shows activation of the 4×CSL-wt-luc plasmid, Panel B shows activation of the CSL-mutant-luc (mt) plasmid, and Panel C shows activation of the 4×CSL-wt-luc and HES1-luc luciferase reporter plasmids as induced by varying amounts of co-transfected ICN1, M2, M-M2, MECT1-MAML1 (M-M1) or MECT1-VP16 (M-VP) plasmids as indicated.

The ability of MECT1-MAML2 and wild-type MAML2 to participate in Notch signaling was further evaluated by examining activation of the Notch target gene, HES1. As shown in FIG. 4, Panels A and B, MAML2 enhanced the Notch ligand (Jagged2) induced activation of the HES1 promoter, but did not enhance activation of a HES1 promoter lacking the two endogenous CSL binding sites (HES1-Δ). Surprisingly, activation of the HES1 promoter by the MECT1-MAML2 chimera was independent of Notch ligand stimulation and was independent of the CSL binding sites within the HES1 promoter (HES1-Δ). The truncated MAML2 (aa 172-1153), which retained the TAD but which lacks the N-terminal exon 1 sequences (AM2), failed to activate HES1. MECT1-MAML2 showed mild activation of the HES7 promoters in U20S cells, HeLa cells and 293 cells, but did not activate transcription of promoters from the telomerase (hTERT), cyclin dependent kinase inhibitors p21 or p27, or the HES5 genes (See, FIG. 5). These findings are indicative of a narrow promoter specificity for the MECT1-MAML2 product. Moreover, the observation that MECT1-MAML2 is unable to form a complex with CSL and can activate the HES1 promoter independent of CSL, indicates that MECT1-MAML2 must function through another unknown binding site on the HES1 promoter. To confirm that MECT1-MAML2 acts independently of CSL, the transcriptional activation of an artificial promoter containing 4 copies of either a wild type or a mutant CSL binding site in front of an SV40 promoter (4×CSL-wt-luc and 4×CSL-mt-luc, respectively) was tested. Previously, transfection of ICN had been shown to activate the wild type promoter in a CSL dependent manner (Hsieh et al., Mol. Cell Biol., 16:952–959 [1996]). As shown in FIG. 6, Panel A, MAML2 (M2) amplified the ICN1-induced activation of the wild type CSL promoter, while MECT1-MAML2 had no stimulatory effect or was inhibitory. No activation was observed with the mutant CSL promoter (See, FIG. 6, Panel B). To examine the contribution of the MAML-like TAD, the MAML2 sequence was replaced with either the equivalent sequence from MAML1 (MECT1-MAML1;M-M1) or with an unrelated transcriptional activator, VP16 (MECT1-VP16; M-VP). As shown in FIG. 6, Panel C, MECT1-MAML1, like MECT1-MAML2, could activate the HES1 promoter independently of ICN1, while MECT1-VP16 had a negligible effect on the HES1 promoter.

Figure 7:
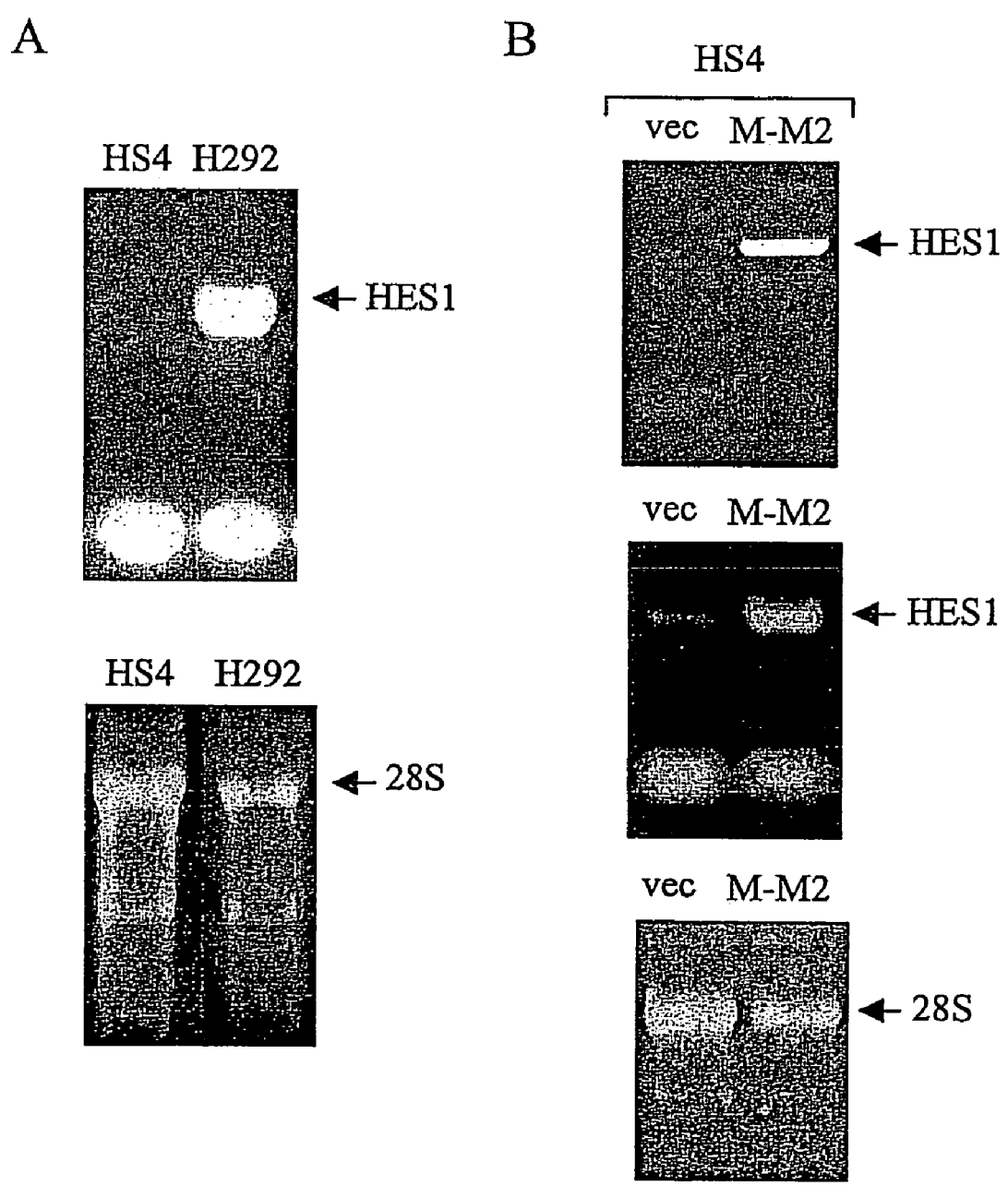
FIG. 7 shows induction of HES1 mRNA by the MECT1-MAML2 product in vivo. Panel A provides the results of an RT-PCR analysis using total RNA extracted from immortalized, normal parotid cells (HS4) or tumor cells (H292). Panel B provides the results of an RT-PCR analysis using total RNA extracted from transiently transfected HS4 cells with either vector alone (vec) or MECT1-MAML2 (M-M2). The 28S ribosomal signals from the RNA samples are indicated.
Figure 8:
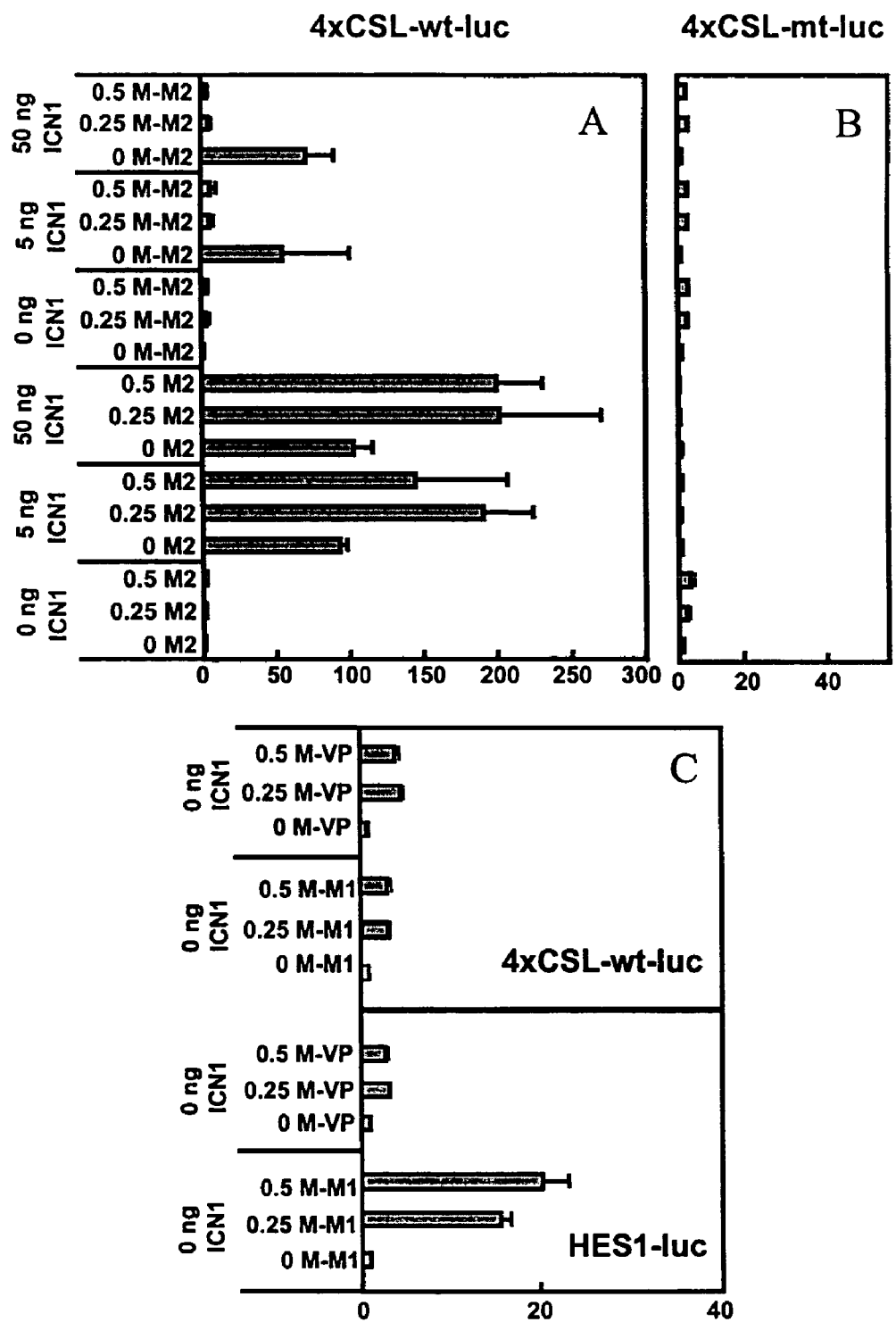
FIG. 8 indicates that MECT1-MAML2 and MECT1-MAML1, but not MECT1-VP16, mediates CSL-independent and ICN-independent activation. Panel A shows activation of the 4×CSL-wt-luc plasmid, Panel B shows activation of the CSL-mutant-luc (mt) plasmid, and Panel C shows activation of the 4×CSL-wt-luc and HES1-luc luciferase reporter plasmids as induced by varying amounts of co-transfected ICN1, M2, M-M2, MECT1-MAML1 (M-M1) or MECT1-VP16 (M-VP) plasmids as indicated.
Figure 9:
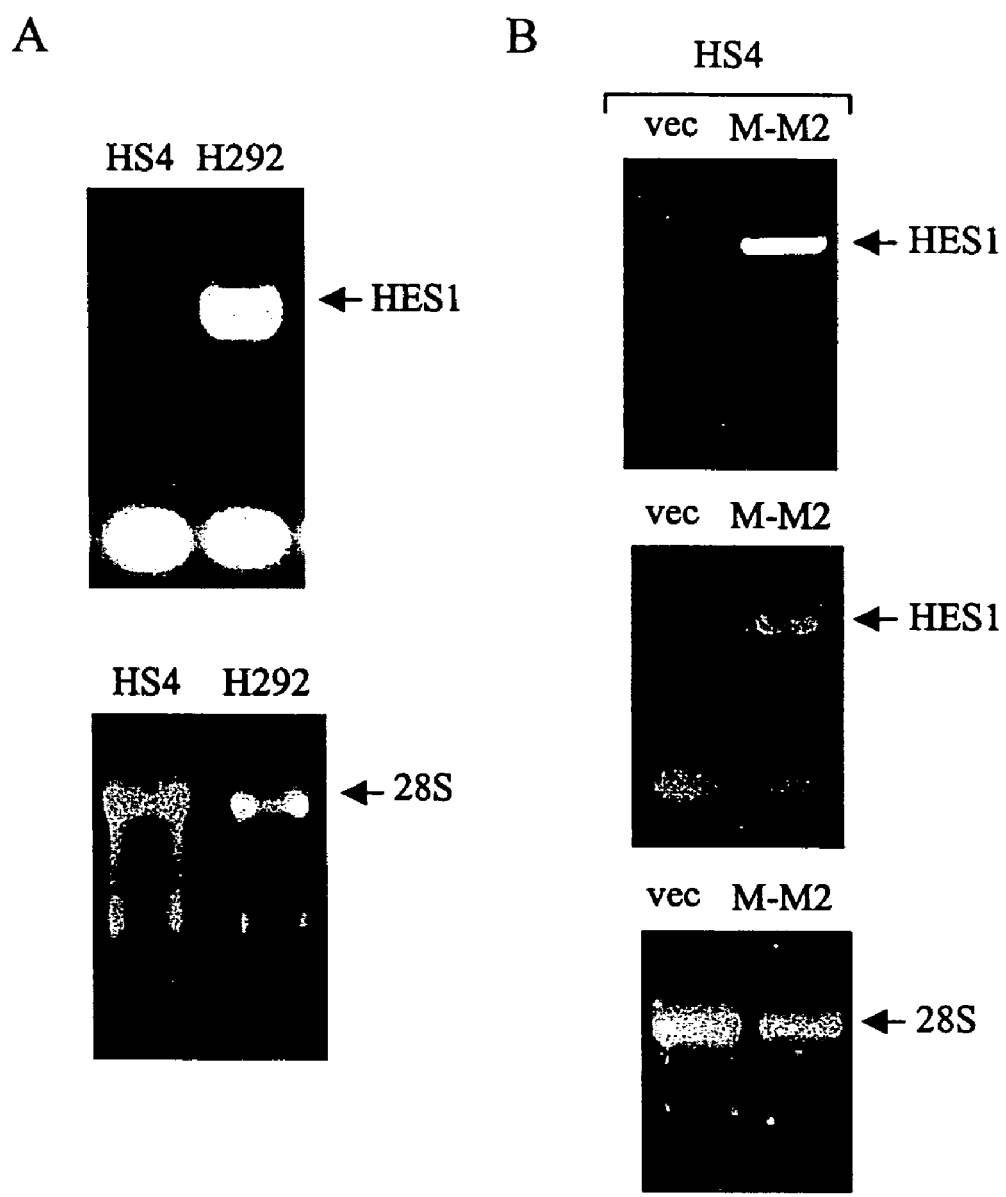
FIG. 9 shows induction of HES1 mRNA by the MECT1-MAML2 product in vivo. Panel A provides the results of an RT-PCR analysis using total RNA extracted from immortalized, normal parotid cells (HS4) or tumor cells (H292). Panel B provides the results of an RT-PCR analysis using total RNA extracted from transiently transfected HS4 cells with either vector alone (vec) or MECT1-MAML2 (M-M2). The 28S ribosomal signals from the RNA samples are indicated.

Confirming the effect of MECT1-MAML2 on the HES1 promoter in vitro, a high HES1 mRNA expression level was detected in the pulmonary MEC line (H292). As shown in FIG. 7, Panel A, this contrasted with the low or absent HES1 mRNA expression level observed in normal, immortalized parotid gland cells (HS4). Transient transfection of the MECT1-MAML2 cDNA into the normal HS4 cells, however, resulted in a rapid induction of HES1 mRNA at 48 hrs as compared to mock-transfected HS4 cells (See, FIG. 7, Panel B).

While chromosomal rearrangements are commonly observed in hematopoietic and mesenchymal stromal tumors, <1% of all epithelial carcinomas show a recurrent, pathogenic chromosomal alteration (Mitelman, Mutat. res., 462:247–253 [2000]). MEC, therefore, represents a new epithelial tumor model system, in which a chimeric gene product disrupts Notch signaling via a novel CSL-independent mechanism. In the case of t(7;9) and T-ALL, the proposed consequence of the translocation is to both deregulate the expression of the mutant Notch1 receptor gene with T-cell receptor βpromoter/enhancer sequences and to express a truncated Notch molecule that can localize to the nucleus and constitutively activate HES family members independent of Notch ligand (Aster and Pear, Curr. Opin. Hematol., 8:237–244 [2001]; and Allman et al., Cell 109S: S1–11 [2002]). While Notch receptors can regulate the differentiation and development of diverse cell lineages, the mechanisms underlying T-cell leukemogenesis are still unknown. During development of the present invention, it has now been demonstrated that the t(11;19) alteration linked with MEC can result in the deregulated expression of a mutant Notch co-activator which in turn can constitutively activate HES1 gene expression. Thus, disruption of NOTCH signaling and/or other functions of the novel MECT1/MAML2 product are contemplated to be an essential component in the genesis of epithelial pulmonary MEC tumors, as well as other human salivary gland tumors associated with the t(11;19) alteration. Therefore, the present invention provides methods and compositions for the diagnosis and treatment for such tumors.

Definitions

As used herein, the terms "purified" and "to purify" refer to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "partially purified" refers to the removal of a moderate portion of the contaminants of a sample to the extent that the substance of interest is recognizable by techniques known to those skilled in the art as accounting for a measurable amount of the mixture.

As used herein, the term "substantially purified" refers to molecules, (e.g., nucleic or amino acid sequences) that are removed from their natural environment, isolated or separated, and are at least 60% free, preferably 75% free, and more preferably 90% free from other components with which they are naturally associated. Furthermore, an "isolated polynucleotide" encompasses a substantially purified polynucleotide.

As used herein, the term "subject" refers to any animal (e.g., a mammal), including, but not limited to, humans, non-human primates, rodents, ovines, bovines, ruminants, lagomorphs, porcines, caprines, equines, canines, felines, aves, etcetera. In some embodiments, the term "subject" refers to the animal from which a biopsy is obtained for testing. Typically, the terms "subject" and "patient" are used interchangeably in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage or type of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, pre-existing non-cancer diseases, and lifestyle.

As used herein, the term "characterizing cancer in subject" refers to the identification of one or more properties of a cancer in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. In preferred embodiments, cancer marker expression refers to MECT1-MAML2 expression, which may be characterized using any suitable method, including but not limited to, those described in illustrative Examples 2–4 below.

As used herein, the term "a reagent capable of specifically detecting" refers to reagents used to monitor the presence and/or quantity of a gene or gene product of interest (e.g., including but not limited to the MECT1-MAML2 chimera of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest As used herein, the terms "detecting a change in gene expression relative to" and "detecting a decrease or an increase in gene expression relative to" refer to measuring the level of expression of a gene (e.g., the level of mRNA or protein) relative to the level in a control sample (e.g., sample lacking a test compound). Gene expression can be measured using any suitable method, including but not limited to, those described herein.

The term "screening" refers to the examination of a sample for a genotype or phenotype of interest. In preferred embodiments, the genotype of interest comprises the t(11; 19)(q14–21; p12–13) translocation, while the phenotype comprises the expression of the MECT1-MAML2 chimera.

The term "tissue sample" refers to specimen comprises cells. In preferred embodiments, the specimen comprises "biopsy material." The term "biopsy" refers to specimen (e.g., salivary gland tissue) collected from a subject for further analysis to establish a diagnosis (e.g., mucoepidermoid carcinoma). Biopsies can be accomplished with a biopsy needle (passed through the skin into the organ in question) or by open surgical incision.

As used herein, the term "salivary gland tumor" refers to an abnormal mass of tissue of any of the saliva-secreting exocrine glands of the oral cavity, that results from excessive cell division (e.g., neoplasm). Salivary gland tumors include but are not limited to mucoepidermoid cancer, pleomorphic adenoma and adenoid cystic carcinoma. The term "mucoepidermoid cancer" refers to a malignant epithelial tumour of glandular tissue, especially the salivary glands, characterised by acini with mucus-producing cells and by the presence of malignant squamous elements. The term "pleomorphic adenoma" refers to a mixed tumour of the salivary gland composed of salivary gland epithelium and fibrous tissue with mucoid or cartilaginous areas. The terms "adenoid cystic carcinoma" and "cylindromatous carcinoma" refer to carcinoma characterised by large epithelial masses containing round, glandlike spaces or cysts which frequently contain mucus or collagen and are bordered by a few or many layers of epithelial cells without intervening stroma, thereby forming a cribriform pattern.

As used herein, the term "instructions for using said kit for screening a tissue sample" refers to the directions for using the reagents contained in the kit for the detection of a t(11;19)(q14–21:p12–13) translocation and/or a MECT1-MAML2 chimera. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

The term "translocation" refers to a rearrangement of a chromosome in which a segment is moved from one location to another, either within the same chromosome or to another chromosome. The is sometimes reciprocal, when one fragment is exchanged for another.

As used herein, the terms "chimera" and "chimeric" refer to a molecule (e.g., gene, transcript or protein) composed of parts that are of different origin and are seemingly incompatible. In preferred embodiments of the present invention the term "chimera" is used in reference to the MECT1-MAML2 chimera formed as a results of a t(11;19)(q14–21: p12–13) translocation. The predicted amino acid sequence of the MECT1-MAML2 chimera is set forth as SEQ ID NO;12.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "antibody" refers a glycoprotein produced by B cells and plasma cells that binds with high specificity to an antigen (usually, but not always, a peptide) or a structurally similar antigen, that generated its production. Antibodies may be produced by any of the known methodologies and may be either polyclonal or monoclonal, and may be of any class (e.g., IgG, IgM, IgA, IgE, IgD).

"Wild-type," as used herein, refers to a gene or gene product which has the characteristics of that gene or gene product when isolated from a naturally occurring source. A wild-type gene is that which is most frequently observed in a population and is thus arbitrarily designed the "normal" or "wild-type" form of the gene.

"Mutant," as used herein, refers to any changes made to a wild-type nucleotide sequence, either naturally or artificially, that produces a translation product that functions with enhanced or decreased efficiency in at least one of a number of ways including, but not limited to, specificity for various interactive molecules, rate of reaction and longevity of the mutant molecule.

"Staining," as used herein, refers to any number of processes known to those in the field that are used to better visualize a specific component(s) and/or feature(s) of a cell or cells.

The terms "cancerous" and "cancer cell" refer to a cell undergoing early, intermediate or advanced stages of multi-step neoplastic progression as known in the art (See e.g., Pitot, in Fundamentals of Oncology, Marcel Dekker (Ed.), New York, pp. 15–28 [1978]). The microscopic features of early, intermediate and advanced stages of neoplastic progression have been described. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell." A dysplastic cell resembles an immature epithelial cell, is generally spatially disorganized within the tissue and has lost its specialized structures and functions. For example, during the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive. Thus, they either invade adjacent tissues, or are shed from the primary site and circulate through the blood and lymph to other locations in the body where they initiate secondary cancers. The term "cancer" or "neoplasia" refers to a plurality of cancer cells.

"Nucleic acid sequence," "nucleotide sequence" and "polynucleotide sequence" as used herein, refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A "variant" of a nucleotide sequence is defined as a nucleotide sequence which differs from the referenced, parent or wild type nucleotide sequence (e.g., by having one or more deletions, insertions, or substitutions that may be detected using hybridization assays or using DNA sequencing). Included within this definition is the detection of alterations to the genomic sequence of the nucleotide sequence. For example, hybridization assays may be used to detect alterations in: (1) the pattern of restriction enzyme fragments capable of hybridizing to a genomic sequence of the first nucleotide sequence (i.e., RFLP analysis); (2) the inability of a selected portion of the first nucleotide sequence to hybridize to a sample of genomic DNA which contains the first nucleotide sequence (e.g., using allele-specific oligonucleotide probes); and (3) improper or unexpected hybridization, such as hybridization to a locus other than the normal chromosomal locus for the first nucleotide sequence (e.g., using fluorescent in situ hybridization (FISH) to metaphase chromosomes spreads, etc.). One example of a variant is a mutated wild type sequence.

The term "portion" when used in reference to a nucleotide sequence refers to fragments of that nucleotide sequence. The fragments may range in size from 5 nucleotide residues to the entire nucleotide sequence minus one nucleic acid residue.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule. As used herein, the terms "vector" and "vehicle" are used interchangeably in reference to nucleic acid molecules that transfer DNA segment(s) from one cell to another.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The terms "expression vector," "expression construct," "expression cassette" and "plasmid," as used herein refer to a recombinant nucleic acid molecule containing a desired coding sequence and appropriate nucleic acid sequences necessary for the expression of the operably linked coding sequence in a particular host organism. The sequences may be either double or single-stranded. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

"Reporter construct," "reporter gene," and "reporter protein," as used herein, refer to nucleic acid or amino acid sequences, as appropriate, that, when expressed in a host cell or organism, may be detected, measured and/or quantitated.

The term "transfection" as used herein refers to the introduction of foreign nucleic acid (e.g., DNA) into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment), and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

In preferred embodiments, an oligonucleotide sequence which is a "homolog" of a first nucleotide sequence is an oligonucleotide sequence which exhibits greater than or equal to 50% identity, and more preferably greater than or equal to 70% identity, to the first nucleotide sequence, when sequences having a length of 10 bp or larger are compared.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

The terms "FISH" and "fluorescence in situ hybridization" refer to a physical mapping approach that uses fluorescent tags to detect hybridization of probes with metaphase chromosomes and with the less-condensed somatic interphase chromatin.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50–90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

The term "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is placed. Examples of heterologous DNA include reporter genes, transcriptional and translational regulatory sequences, selectable marker proteins (e.g., proteins which confer drug resistance), etc.

"Amplification" is defined herein as the production of additional copies of a nucleic acid sequence and is generally carried out using polymerase chain reaction technologies well known in the art (See e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, and which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The terms "Western blot" and "immunoblot" refer to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of enzyme or radiolabeled antibodies.

As used herein, the term "microarray" refers to analysis of individual recombinant clones (e.g., cosmid, YAC, BAC, plasmid or other vectors) that are placed on a two-dimensional solid support (e.g., microscope slide). Each primary clone can be identified on the support by virtue of its location (row and column) on the solid support. Arrayed libraries of clones can be screened with RNA obtained from a specimen of interest upon conjugation of a fluorochrome.

The terms "IFA" and "immunofluorescence analysis" refer to a test or technique in which one or other component of an immunological reaction is made fluorescent by coupling with a fluorochrome such as fluorescein, phycoerythrin or rhodamine so that the occurrence of the reaction can be detected as a fluorescing antigen-antibody complex.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "sense oligonucleotide" refers to an oligonucleotide having a nucleic acid sequence which corresponds to that of an mRNA. In contrast, the term "antisense oligonucleotide" refers to an oligonucleotide having a nucleic acid sequence which corresponds to the complement of mRNA. the strand of DNA which is used during transcription to make mRNA. The mRNA made thus has the sequence of the antisense strand of DNA, and it codes for a sense strand of polypeptide (which eventually becomes a protein or part of a protein) during translation.

The terms "restriction endonucleases" and "restriction enzymes," as used herein, refer to bacterial enzymes, each of which cut double- or single-stranded nucleic acid at or near a specific nucleotide sequence.

As used herein, the term "an oligonucleotide having a nucleotide sequence encoding a gene" means a nucleic acid sequence comprising the coding region of a gene (i.e. the nucleic acid sequence which encodes a gene product). The coding region may be present in either a cDNA, genomic DNA or RNA form. When present in a DNA form, the oligonucleotide may be single-stranded (i.e., the sense strand) or double-stranded. Suitable control elements (e.g., enhancers, promoters, splice junctions, polyadenylation signals, etc.) may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, or other sequences, or a combination of both endogenous and exogenous control elements.

Transcriptional control signals in eukaryotes comprise "enhancer" elements. Enhancers consist of short arrays of DNA sequences that interact specifically with cellular proteins involved in transcription (See, Maniatis et al., Science 236:1237 [1987]). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (See e.g., Sambrook et al., *Molecular Cloning: A Laboratory Manual,* 2nd ed., Cold Spring Harbor Laboratory Press, New York, pp. 16.7–16.8 [1989]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The terms "promoter," "promoter element," and "promoter sequence" as used herein, refer to a DNA sequence which when placed at the 5' end of (i.e., precedes) an oligonucleotide sequence, is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid (e.g., "an isolated oligonucleotide") refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Typically, isolated nucleic acid can be readily identified (if desired) by a variety of techniques (e.g., hybridization, dot blotting, etc.). When an isolated nucleic acid or oligonucleotide is to be utilized to express a protein, the oligonucleotide contains at a minimum, the sense or coding strand (i.e., the oligonucleotide may be single-stranded). Alternatively, it may contain both the sense and anti-sense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the terms "structural gene" and "structural nucleotide sequence" refer to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript;

introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

Experimental

The following examples are provided in order to demonstrate and further illustrate certain preferred embodiments and aspects of the present invention and are not to be construed as limiting the scope thereof In the experimental disclosure which follows, the following abbreviations apply: ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); aa (amino acid); bp (base pair); kb (kilobase pair); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); µM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl)aminomethane); w/v (weight to volume); v/v (volume to volume); BAC (bacterial artificial chromosome); and YAC (yeast artificial chromosome).

Materials and equipment were obtained from the following sources: Ambion (Ambion, Inc., Austin, Tex.); Amersham (Amersham Pharmacia Biotechnology, Inc., Piscataway, N.J.); Amicon (Amicon, Inc., Beverly, Mass.); ATCC (American Type Culture Collection, Rockville, Md.);

Applied Spectral Imaging (Applied Spectral Imaging, Carlsbad, Calif.); Becton Dickinson (Becton Dickinson Labware, Lincoln Park, N.J.); BioRad (BioRad, Richmond, Calif.); Chroma (Chroma Technology, Brattleboro, Vt.); Clontech (Clontech Laboratories, Palo Alto, Calif.); Difco (Difco Laboratories, Detroit, Mich.); GIBCO BRL or Gibco BRL (Life Technologies, Inc., Gaithersburg, Md.); HyClone (HyClone, Logan, Utah); ICN (ICN Pharmaceuticals, Inc., Costa Mesa, Calif.); Invitrogen (Invitrogen Corp., San Diego, Calif.); Leica Microsystems (Leica Microsystems Imaging Solutions, Cambridge, United Kingdom); Leica (Leica, Wetzlar, Germany); Molecular Probes (Molecular Probes, Eugene, Oreg.); New England Biolabs (New England Biolabs, Inc., Beverly, Mass.); Novagen (Novagen, Inc., Madison, Wis.); Oakland BAC/PAC Resources (Oakland BAC/PAC Resources, Oakland, Calif.); Perkin Elmer or PE (Perkin Elmer Applied Biosystems, Foster City, Calif.); Photometrics (Photometrics, Tucson, Ariz.); Promega (Promega Corporation, Madison, Wis.); Qiagen (Qiagen Inc., Valencia, Calif.); Research Genetics (Research Genetics, Huntsville, Ala.); Roche (Hoffmann La Roche, Indianapolis, Ind.); Sigma Aldrich (Sigma Aldrich Chemical Co., St. Louis, Mo.); Stratagene (Stratagene Cloning Systems, La Jolla, Calif.); Vector (Vector Laboratories, Burlingame, Calif.); and Vysis (Vysis, Downers Grove, Ill.).

EXAMPLE 1

Tumor Samples

In this Example, the tumor samples used during the development of the present invention are described. The H292 and H3118 (pulmonary MEC), the H727 (pulmonary carcinoid), and H2009 (non-small cell lung cancer) tumor cell lines were generated from patient biopsy samples at the National Naval Medical Center as known in the art (See, Carney et al., Cancer Res., 45:2913–23 [1985]; and Modi et al., Oncogene 19:4632–9 [2000]) using an IRB-approved tissue procurement protocol. The pulmonary MEC tumor sample (MECT #A) was obtained as an anonymous tumor sample approved for inclusion in this study by the NIH Office of Human Subjects Research. Human U2OS osteosarcoma cells were cultured in Dulbecco's modified Eagle's medium (DMEM) containing 10% Fetalclone I serum (HyClone). COS7 cells were cultured in RPMI 1640 medium supplemented with 10% FCS. NIH 3T3 cell transduced with the pBABE retrovirus encoding Jagged 2, or empty pBABE retrovirus, were maintained in DMEM containing 10% FCS and 1 mg/ml puromycin.

EXAMPLE 2

Spectral Karyotyping

In this Example, the spectral karyotyping methods used in the development of the present invention are briefly described (See, Tonon et al., Genes Chromosomes Cancer 27:418–23 [2000]). Specific chromosomes, kindly provided by Dr. Thomas Ried, were obtained by high-resolution flow sorting, and then amplified using two consecutive rounds of degenerate oligo-primed (DOP)-PCR amplification. Methods commonly used and widely known in the art were used for the spectral karyotyping experiments.

Spectrum Orange (Vysis), Rhodamine 110 (Perkin Elmer), and Texas Red (Molecular Probes) were used for the direct labeling of chromosomes, whereas Biotin-16-dUTP and Digoxigenin-11-DUTP (Roche) were used for the indirect labeling of chromosomes. After hybridization, biotin was detected with Avidin-Cy5 (Amersham) and digoxigenin-11-dUTP with mouse anti-digoxin (Sigma) followed by sheep anti-mouse antibodies custom-conjugated to Cy5.5 (Amersham). The slides were counterstained with 4,6-diamidino-2-phenylindole (DAPI, Sigma) and covered with antifade solution (Vector). Spectral images were acquired with an SD200 SpectraCube system (Applied Spectral Imaging) mounted on a Leica DMRBE microscope (Leica) through a custom-designed triple bandpass optical filter (SKY v.3; Chroma). Spectrum-based classification of the raw spectral images was performed using SKYView 1.6 software (Applied Spectral Imaging).

EXAMPLE 3

Fluorescence in Situ Hybridization (FISH) Analysis

In this Example, the FISH analysis used during the development of the present invention is described. BAC clones were purchased from Research Genetics, Oakland BAC/PAC Resources, or provided by Dr. Raluca Jonescu (RP11-16K5). For the FISH analysis, BAC clones were labeled by nick translation. BAC clones RP11-676L3 and RP11-16K5 were used to identify translocations. Image acquisition was performed using a Sensys CCD camera (Photometrics), and Q-FISH software (Leica Microsystems Imaging Solutions). Using standard FISH protocols, specific translocation events were detected. Additional experiments to identify translocation using a single probe were also conducted using methods known in the art.

EXAMPLE 4

Nucleic Acid Analysis

In this Example, nucleic acid analysis methods used during the development of the present invention are described. Total RNA was obtained from tumor samples using guanidine isothiocyanate methodology as known in the art (See, Sambrook et al., *Molecular cloning: a laboratory manual*. Cold Spring Harbor Press, Cold Spring Harbor, N.Y. [1989]), and subjected to 5' and 3' RACE using conditions as recommended by the manufacturer (SmartRace, Clontech). RT-PCR with gene-specific oligonucleotides for MECT/MAML2 was performed as recommended by the manufacturer (Amersham Pharmacia). The method utilized first-strand cDNA from oligo-dT primers, followed by PCR using gene-specific oligonucleotides. The PCR conditions included a denaturation step at 95° C. for 30 seconds, annealing at 55° C. for 30 seconds, and extension at 72° C. for 30 seconds.

In these methods, the oligonucleotide primers used to detect specific MECT1/MAML2 fusion mRNA in mucoepidermoid tumors had the following sequences: MECT1 Exon 1 Sense, 5'-CGA GAA GAT GGC GAC TTC GAA CA-3' (SEQ ID NO:10) and MAML2 Exon 2 Antisense, 5'-CCA TTG GGT CGC TTG CTG TTG GCA GGA G-3' (SEQ ID NO:11). RT-PCR produced a distinct 203 bp signal in all mucoepidermoid tumor samples tested. However, this signal was not detected in other tumor types tested. It is contemplated that this signal is detectable in all tumor samples carrying the t(11;19) translocation described herein.

The MAML2, MECT1-MAML2, and MAML2 (172–1153) cDNAs were subcloned into a CMV-2 driven expression vector in-frame with the sequence encoding the FLAG tag (pFLAG-CMV2) and into the pEGFP-C3 (Clontech) and pBIND (Promega) vectors. All constructs were confirmed by nucleotide sequencing and immunoblotting. The full-length MECT1-MAML2 was cloned, as a Sal I-Not I fragment, into pEGFP-C3 and pBIND. HA-epitope-tagged ICN1 and myc-epitope tagged CSL have been previously described (Wu et al., supra [2000]). HES1-luc contains the −194 to +160 promoter fragment of the HES1 gene cloned upstream of the firefly luciferase gene in the pGL2-basic vector (Jarriault et al., Nature 377:355–358 [1995]), and HES1-Δ-luc, derived from HES1-luc, has a deletion removing the two CSL binding sites. hTERT-luc was obtained by cloning 2.5 kb of the hTERT promoter (Greenberg et al., Oncogene 18:1219–1226 [1999]) into pGL3-basic vector. p21-luc (Tang et al., J. Biol. Chem., 273:29156–29163 [1998]), p27-luc (Kwon et al., Gene 180:113–120 [1996]), HES-5-luc (Beatus et al., Development 126:3925–3935 [1999]) and HES-7 (Bessho et al., Genes Cell 6:175–185 [2001]) have been previously described. pRL-TK (Promega) which contains a *Renilla* luciferase insert under control of the thymidine kinase promoter, was used to normalize firefly luciferase activity in order to determine transfection efficiency. pSG5-luc (Promega) is a firefly luciferase reporter plasmid that contains five copies of the GAL4 binding site upstream of a minimal TATA box.

EXAMPLE 5

Protein Studies

This Example describes the materials and methods used immunofluorescence analysis and immunoprecipitation. The following antibodies were obtained from commercial sources: mouse anti-Flag antibody (clone M2, Sigma); mouse anti-HA antibody (clone HA. 11, Babco); mouse anti-Myc antibody (clone 9E10, Clontech); horseradish peroxidase (HRP)-coupled goat anti-mouse antibody (Amersham). Transfections were carried out using Superfect transfection reagent (QIAGEN) according to the manufacturer's instructions. At 48 hrs post-transfection, cells were washed with ice-cold PBS and lysed in situ with a solution containing 20 mM Tris (pH 8.0), 150 mM NaCl, 1% NP-40 (w/v), 10% glycerol (w/v), 100 mM NaF, 1 mM phenylmethylsulfonyl fluoride (PMSF), 20 µg/ml aprotinin, 1 mM sodium orthovanadate ($Na_3VO_4$), and 40 µg/ml leupeptin. After incubation on ice for 30 min, cell lysates were centrifuged at 12,000 g for 15 min at 4° C. Cleared lysates were incubated with anti-Flag antibody (M2 at 1:500) and anti-mouse IgG agarose (Sigma) for 4 h or overnight at 4° C. The washed pellets were then subjected to SDS-PAGE and western blotting using the indicated antibodies. Washed membranes were incubated with HRP-coupled secondary antibodies for 1 hr, washed again and stained using a chemiluminescent reagent (ECL, Amersham).

EXAMPLE 6

Luciferase Assays

In this Example, the materials and methods for analysis of transcription are described. Briefly, cells were seeded on the six-well plates at $1 \times 10^5$ cells per well (U2OS and HeLa cells), or at $2 \times 10^5$ cells per well (293 cells) 1 day prior to transient co-transfection using the indicated plasmid DNA combinations and concentrations. In these experiments, the total plasmids concentration was kept constant by adding appropriate quantities of vectors without inserts. Transfected cells were harvested 48 hrs post-transfection and luciferase activities were measured in a Berthold luminometer (Lumat LB9507) using the dual luciferase reporter assay system (Promega) as directed by the manufacturer. Relative luciferase activities were normalized to *Renilla* luciferase activity.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A method of screening a tissue sample from a mucoepidermoid cancer for a t(11;19)(q14–21; p12–13) translocation, comprising
   (a) detecting the presence of a MECT1-MAML2 DNA in a tissue sample from a mucoepidermoid cancer by (i) amplifying at least a portion of said MECT1-MAML2 DNA by polymerase chain reaction or (ii) Southern blot, or
   (b) detecting the presence of a MECT1-MAML2 mRNA in a tissue sample by (i) amplifying at least a portion of a MECT1-MAML2 mRNA by reverse-transcriptase polymerase chain reaction or (ii) Northern blot.

2. The method of claim 1, wherein said tissue sample comprises biopsy material.

3. The method of claim 2, wherein said biopsy material comprises cells from a salivary gland tumor.

4. The method of claim 1, wherein the detecting is by amplifying at least a portion of said MECT1-MAML2 DNA by polymerase chain reaction.

5. The method of claim 1, wherein said detecting is by Southern blot.

6. The method of claim 1, wherein said detecting is by amplifying at least a portion of a MECT1-MAML2 mRNA by reverse-transcriptase polymerase chain reaction.

7. The method of claim 1, wherein said detecting is by Northern blot.

8. A method of screening a tissue sample from a mucoepidermoid cancer for a t(11;19)(q14–21;p12–13) translocation, comprising detecting the presence of a MECT1-MAML2 chimeric protein in a tissue sample from a mucoepidermoid cancer.

9. The method of claim 8, wherein said detecting is by immunoblot.

10. The method of claim 8, wherein said detecting is by inununofluorescence analysis.

11. The method of claim 8, wherein said tissue sample comprises biopsy material.

12. The method of claim 11, wherein said biopsy material comprises cells from a salivary gland tumor.

* * * * *

SEQUENCE LISTING

```
<160> NUMBER OF SEQ ID NOS: 12

<210> SEQ ID NO 1
<211> LENGTH: 1153
<212> TYPE: PRT
<213> ORGANISM: Homo sapiens

<400> SEQUENCE: 1

Met Gly Asp Thr Ala Pro Pro Gln Ala Pro Ala Gly Gly Leu Gly Gly
1               5                   10                  15

Ala Ser Gly Ala Gly Leu Leu Gly Gly Gly Ser Val Thr Pro Arg Val
            20                  25                  30

His Ser Ala Ile Val Glu Arg Leu Arg Ala Arg Ile Ala Val Cys Arg
        35                  40                  45

Gln His His Leu Ser Cys Glu Gly Arg Tyr Glu Arg Gly Arg Ala Glu
    50                  55                  60
```

-continued

```
Ser Ser Asp Arg Glu Arg Glu Ser Thr Leu Gln Leu Leu Ser Leu Val
 65                  70                  75                  80

Gln His Gly Gln Gly Ala Arg Lys Ala Gly Lys His Thr Lys Ala Thr
                 85                  90                  95

Ala Thr Ala Ala Thr Thr Thr Ala Pro Pro Pro Pro Pro Ala Ala Pro
            100                 105                 110

Pro Ala Ala Ser Gln Ala Ala Ala Thr Ala Ala Pro Pro Pro Pro Pro
        115                 120                 125

Asp Tyr His His His His Gln Gln His Leu Leu Asn Ser Ser Asn Asn
130                 135                 140

Gly Gly Ser Gly Gly Ile Asn Gly Glu Gln Gln Pro Pro Ala Ser Thr
145                 150                 155                 160

Pro Gly Asp Gln Arg Asn Ser Ala Leu Ile Ala Leu Gln Gly Ser Leu
                165                 170                 175

Lys Arg Lys Gln Val Val Asn Leu Ser Pro Ala Asn Ser Lys Arg Pro
            180                 185                 190

Asn Gly Phe Val Asp Asn Ser Phe Leu Asp Ile Lys Arg Ile Arg Val
        195                 200                 205

Gly Glu Asn Leu Ser Ala Gly Gln Gly Gly Leu Gln Ile Asn Asn Gly
210                 215                 220

Gln Ser Gln Ile Met Ser Gly Thr Leu Pro Met Ser Gln Ala Pro Leu
225                 230                 235                 240

Arg Lys Thr Asn Thr Leu Pro Ser His Thr His Ser Pro Gly Asn Gly
                245                 250                 255

Leu Phe Asn Met Gly Leu Lys Glu Val Lys Lys Glu Pro Gly Glu Thr
            260                 265                 270

Leu Ser Cys Ser Lys His Met Asp Gly Gln Met Thr Gln Glu Asn Ile
        275                 280                 285

Phe Pro Asn Arg Tyr Gly Asp Asp Pro Gly Glu Gln Leu Met Asp Pro
290                 295                 300

Glu Leu Gln Glu Leu Phe Asn Glu Leu Thr Asn Ile Ser Val Pro Pro
305                 310                 315                 320

Met Ser Asp Leu Glu Leu Glu Asn Met Ile Asn Ala Thr Ile Lys Gln
                325                 330                 335

Asp Asp Pro Phe Asn Ile Asp Leu Gly Gln Gln Ser Gln Arg Ser Thr
            340                 345                 350

Pro Arg Pro Ser Leu Pro Met Glu Lys Ile Val Ile Lys Ser Glu Tyr
        355                 360                 365

Ser Pro Gly Leu Thr Gln Gly Pro Ser Gly Ser Pro Gln Leu Arg Pro
370                 375                 380

Pro Ser Ala Gly Pro Ala Phe Ser Met Ala Asn Ser Ala Leu Ser Thr
385                 390                 395                 400

Ser Ser Pro Ile Pro Ser Val Pro Gln Ser Gln Ala Gln Pro Gln Thr
                405                 410                 415

Gly Ser Gly Ala Ser Arg Ala Leu Pro Ser Trp Gln Glu Val Ser His
            420                 425                 430

Ala Gln Gln Leu Lys Gln Ile Ala Ala Asn Arg Gln His Ala Arg
        435                 440                 445

Met Gln Gln His Gln Gln His Gln Pro Thr Asn Trp Ser Ala Leu
    450                 455                 460

Pro Ser Ser Ala Gly Pro Ser Gly Pro Phe Gly Gln Glu Lys Ile
465                 470                 475                 480

Pro Ser Pro Ser Phe Gly Gln Gln Thr Phe Ser Pro Gln Ser Ser Pro
```

-continued

```
                485                 490                 495
Met Pro Gly Val Ala Gly Gly Ser Gly Gln Ser Lys Val Met Ala Asn
            500                 505                 510
Tyr Met Tyr Lys Ala Gly Pro Ser Ala Gln Gly Gly His Leu Asp Val
            515                 520                 525
Leu Met Gln Gln Lys Pro Gln Asp Leu Ser Arg Ser Phe Ile Asn Asn
            530                 535                 540
Pro His Pro Ala Met Glu Pro Arg Gln Gly Asn Thr Lys Pro Leu Phe
545                 550                 555                 560
His Phe Asn Ser Asp Gln Ala Asn Gln Gln Met Pro Ser Val Leu Pro
            565                 570                 575
Ser Gln Asn Lys Pro Ser Leu Leu His Tyr Thr Gln Gln Gln Gln Gln
            580                 585                 590
Gln Gln Gln Gln Gln Gln Gln Gln Gln Gln Gln Gln Gln Gln Gln Gln
            595                 600                 605
Gln Gln Gln Gln Gln Gln Gln Gln Gln Ser Ser Ile Ser Ala Gln
            610                 615                 620
Gln Gln Gln Gln Gln Gln Ser Ser Ile Ser Ala Gln Gln Gln Gln Gln
625                 630                 635                 640
Gln Gln Gln Gln Gln Gln Gln Gln Gln Gln Gln Gln Gln Gln Gln Gln
            645                 650                 655
Gln Gln Gln Gln Gln Pro Ser Ser Gln Pro Ala Gln Ser Leu Pro
            660                 665                 670
Ser Gln Pro Leu Leu Arg Ser Pro Leu Pro Leu Gln Gln Lys Leu Leu
            675                 680                 685
Leu Gln Gln Met Gln Asn Gln Pro Ile Ala Gly Met Gly Tyr Gln Val
            690                 695                 700
Ser Gln Gln Gln Arg Gln Asp Gln His Ser Val Val Gly Gln Asn Thr
705                 710                 715                 720
Gly Pro Ser Pro Ser Pro Asn Pro Cys Ser Asn Pro Asn Thr Gly Ser
            725                 730                 735
Gly Tyr Met Asn Ser Gln Gln Ser Leu Leu Asn Gln Gln Leu Met Gly
            740                 745                 750
Lys Lys Gln Thr Leu Gln Arg Gln Ile Met Glu Gln Lys Gln Gln Leu
            755                 760                 765
Leu Leu Gln Gln Gln Met Leu Ala Asp Ala Glu Lys Ile Ala Pro Gln
            770                 775                 780
Asp Gln Ile Asn Arg His Leu Ser Arg Pro Pro Asp Tyr Lys Asp
785                 790                 795                 800
Gln Arg Arg Asn Val Gly Asn Met Gln Pro Thr Ala Gln Tyr Ser Gly
            805                 810                 815
Gly Ser Ser Thr Ile Ser Leu Asn Ser Asn Gln Ala Leu Ala Asn Pro
            820                 825                 830
Val Ser Thr His Thr Ile Leu Thr Pro Asn Ser Ser Leu Leu Ser Thr
            835                 840                 845
Ser His Gly Thr Arg Met Pro Ser Leu Ser Thr Ala Val Gln Asn Met
            850                 855                 860
Gly Met Tyr Gly Asn Leu Pro Cys Asn Gln Pro Asn Thr Tyr Ser Val
865                 870                 875                 880
Thr Ser Gly Met Asn Gln Leu Thr Gln Gln Arg Asn Pro Lys Gln Leu
            885                 890                 895
Leu Ala Asn Gln Asn Asn Pro Met Met Pro Arg Pro Pro Thr Leu Gly
            900                 905                 910
```

-continued

```
Pro Ser Asn Asn Asn Val Ala Thr Phe Gly Ala Gly Ser Val Gly
        915                 920                 925

Asn Ser Gln Gln Leu Arg Pro Asn Leu Thr His Ser Met Ala Ser Met
        930                 935                 940

Pro Pro Gln Arg Thr Ser Asn Val Met Ile Thr Ser Asn Thr Thr Ala
945                 950                 955                 960

Pro Asn Trp Ala Ser Gln Glu Gly Thr Ser Lys Gln Gln Glu Ala Leu
                965                 970                 975

Thr Ser Ala Gly Val Arg Phe Pro Thr Gly Thr Pro Ala Ala Tyr Thr
        980                 985                 990

Pro Asn Gln Ser Leu Gln Gln Ala Val Gly Ser Gln Gln Phe Ser Gln
        995                 1000                1005

Arg Ala Val Ala Pro Pro Asn Gln Leu Thr Pro Ala Val Gln Met
    1010                1015                1020

Arg Pro Met Asn Gln Met Ser Gln Thr Leu Asn Gly Gln Thr Met
    1025                1030                1035

Gly Pro Leu Arg Gly Leu Asn Leu Arg Pro Asn Gln Leu Ser Thr
    1040                1045                1050

Gln Ile Leu Pro Asn Leu Asn Gln Ser Gly Thr Gly Leu Asn Gln
    1055                1060                1065

Ser Arg Thr Gly Ile Asn Gln Pro Pro Ser Leu Thr Pro Ser Asn
    1070                1075                1080

Phe Pro Ser Pro Asn Gln Ser Ser Arg Ala Phe Gln Gly Thr Asp
    1085                1090                1095

His Ser Ser Asp Leu Ala Phe Asp Phe Leu Ser Gln Gln Asn Asp
    1100                1105                1110

Asn Met Gly Pro Ala Leu Asn Ser Asp Ala Asp Phe Ile Asp Ser
    1115                1120                1125

Leu Leu Lys Thr Glu Pro Gly Asn Asp Asp Trp Met Lys Asp Ile
    1130                1135                1140

Asn Leu Asp Glu Ile Leu Gly Asn Asn Ser
    1145                1150

<210> SEQ ID NO 2
<211> LENGTH: 593
<212> TYPE: PRT
<213> ORGANISM: Homo sapiens

<400> SEQUENCE: 2

Met Ala Thr Ser Asn Asn Pro Arg Lys Phe Ser Glu Lys Ile Ala Leu
1               5                   10                  15

His Asn Gln Lys Gln Ala Glu Glu Thr Ala Ala Phe Glu Glu Val Met
            20                  25                  30

Lys Asp Leu Ser Leu Thr Arg Ala Ala Arg Leu Gln Leu Gln Lys Ser
        35                  40                  45

Gln Tyr Leu Gln Leu Gly Pro Ser Arg Gly Gln Tyr Tyr Gly Gly Ser
    50                  55                  60

Leu Pro Asn Val Asn Gln Ile Gly Ser Gly Thr Met Asp Leu Pro Phe
65                  70                  75                  80

Gln Thr Pro Phe Gln Ser Ser Gly Leu Asp Thr Ser Arg Thr Thr Arg
                85                  90                  95

His His Gly Leu Val Asp Arg Val Tyr Arg Glu Arg Gly Arg Leu Gly
            100                 105                 110

Ser Pro His Arg Arg Pro Leu Ser Val Asp Lys His Gly Arg Gln Ala
```

```
            115                 120                 125
Asp Ser Cys Pro Tyr Gly Thr Met Tyr Leu Ser Pro Ala Asp Thr
    130                 135                 140
Ser Trp Arg Arg Thr Asn Ser Asp Ser Ala Leu His Gln Ser Thr Met
145                 150                 155                 160
Thr Pro Thr Gln Pro Glu Ser Phe Ser Gly Ser Gln Asp Val His
                165                 170                 175
Gln Lys Arg Val Leu Leu Thr Val Pro Gly Met Glu Glu Thr Thr
            180                 185                 190
Ser Glu Ala Asp Lys Asn Leu Ser Lys Gln Ala Trp Asp Thr Lys Lys
            195                 200                 205
Thr Gly Ser Arg Pro Lys Ser Cys Glu Val Pro Gly Ile Asn Ile Phe
    210                 215                 220
Pro Ser Ala Asp Gln Glu Asn Thr Thr Ala Leu Ile Pro Ala Thr His
225                 230                 235                 240
Asn Thr Gly Gly Ser Leu Pro Asp Leu Thr Asn Ile His Phe Pro Ser
                245                 250                 255
Pro Leu Pro Thr Pro Leu Asp Pro Glu Glu Pro Thr Phe Pro Ala Leu
            260                 265                 270
Ser Ser Ser Ser Ser Thr Gly Asn Leu Ala Ala Asn Leu Thr His Leu
    275                 280                 285
Gly Ile Gly Gly Ala Gly Gln Gly Met Ser Thr Pro Gly Ser Ser Pro
    290                 295                 300
Gln His Arg Pro Ala Gly Val Ser Pro Leu Ser Leu Ser Thr Glu Ala
305                 310                 315                 320
Arg Arg Gln Gln Ala Ser Pro Thr Leu Ser Pro Leu Ser Pro Ile Thr
                325                 330                 335
Gln Ala Val Ala Met Asp Ala Leu Ser Leu Glu Gln Gln Leu Pro Tyr
            340                 345                 350
Ala Phe Phe Thr Gln Ala Gly Ser Gln Gln Pro Pro Gln Pro Gln
    355                 360                 365
Pro Pro Pro Pro Pro Pro Ala Ser Gln Gln Pro Pro Pro Pro Pro
    370                 375                 380
Pro Pro Gln Ala Pro Val Arg Leu Pro Pro Gly Gly Pro Leu Leu Pro
385                 390                 395                 400
Ser Ala Ser Leu Thr Arg Gly Pro Gln Pro Pro Leu Ala Val Thr
                405                 410                 415
Val Pro Ser Ser Leu Pro Gln Ser Pro Glu Asn Pro Gly Gln Pro
            420                 425                 430
Ser Met Gly Ile Asp Ile Ala Ser Ala Pro Ala Leu Gln Gln Tyr Arg
            435                 440                 445
Thr Ser Ala Gly Ser Pro Ala Asn Gln Ser Pro Thr Ser Pro Val Ser
    450                 455                 460
Asn Gln Gly Phe Ser Pro Gly Ser Ser Pro Gln Leu Glu Gln Phe Asn
465                 470                 475                 480
Met Met Glu Asn Ala Ile Ser Ser Ser Leu Tyr Ser Pro Gly Ser
                485                 490                 495
Thr Leu Asn Tyr Ser Gln Ala Ala Met Met Gly Leu Thr Gly Ser His
            500                 505                 510
Gly Ser Leu Pro Asp Ser Gln Gln Leu Gly Tyr Ala Ser His Ser Gly
    515                 520                 525
Ile Pro Asn Ile Ile Leu Thr Val Thr Gly Glu Ser Pro Pro Ser Leu
    530                 535                 540
```

Ser Lys Glu Leu Thr Ser His Arg Gly His Leu Pro Asp Gly Pro
545                 550                 555                 560

Val Ser Gly His Ala Gly Thr Leu Pro Leu Ser Arg Pro Asp Gly Ala
            565                 570                 575

Ser Pro Ala Arg Gly Arg Pro Cys Ser Val Pro Arg Gln Arg Pro Ser
            580                 585                 590

Leu

<210> SEQ ID NO 3
<211> LENGTH: 5419
<212> TYPE: DNA
<213> ORGANISM: Homo sapiens

<400> SEQUENCE: 3

```
ctccctctcc tatcggagca caatgaaagc ctgtgtatcg ccgtgactcc gggcgggagc      60
cagtgtcagc aaagcggcta acaacagacg agaaagagaa aggaaaatac aagctacttt     120
ttttttccat ctataaagcg gagcaaatac aggagataga accagattgc ttattgcgag     180
tccagaccct cagatccact ggccggggat ggaatgtaca aaagtggaca gaaagtggc      240 tggacatgac tcggtgcaat ttgctggaag tttgtaagtt tgaccatcgt ttgtaaatta     300
ctctcggaag agtttgtctc tcttgatact gtattagaat agagccgggg gtgaggaata     360
gaaacgtaag cgggaaagaa aaaatgtgt tgaaggatct ctctcagtgg ctagcgactt      420
aagattgctt tcatttaag gctaggaaac cttagaggga gtgaggattt taccggtgat      480
tggattagct gaagaaaaaa gcatggtcca aaagtccaat tactgacatt gttaacagtt     540
gaaaagctgt ctccctcttt tgggagaaga caacatccta cagtacccca aagaggagaa     600
aacaccggag cgaaaggaaa gggaggaaaa attaaaagcc aaaagacagt ctcccttgat     660
ttttgcacat tttgaacagt gacttaaaca tcttctgaaa cagcactgtt ttgttttgtt     720
ttggtttttt atttaacctg aggaaaagtc aaggctgctg gttacataga catggtagaa     780
atgtgtttct ctgcagaaac atccccataa agaattgtcg gaaacaacta ggtgaggggg     840
agtcctctct attaatacct ctctcaatac cttttgctgt gtgtttctgt ctcttgctgg     900
acaatccctg aattcttgat ctaaccccca gatcgtgtgt ttacaaagta cctagtggct     960
cttgtcagct tggtggagga aaaaaaatcc accaactctg tccaacttct ccagagctgt    1020
caaatgcaat tagagtaagt taatcagggt ttgtttccaa cttatcctcc ccccagttgg    1080
tttctattct ttctccccac cctcttttta ctaactcccc tccccacaa cttctccacg     1140 gctcccccac aacctctgaa gacctctatt catgtggccc tgaacactga gctcacattg    1200
tcaaaaacag acttgcctgc aatagccagc agtagcctct ttccacctca ccatcccaga    1260
ggcagcaatc attgtgtccg gtaagatggg ggacacagcg ccccgcagg ccccgcagg      1320 agggctaggg ggggcctctg gggcggggct ccttggaggg ggctcagtca ccccgagagt    1380
gcacagtgct atcgtggagc gcctccgggc tcggatcgct gtctgccgcc aacaccacct    1440
gagctgtgaa ggacgatatg aacgaggtag ggccgagagc tcagaccggg aaagagaaag    1500
caccttgcag ctcctgagcc ttgtacagca tggccagggg gcaaggaaag ctggcaaaca    1560
caccaaggcc accgccactg ctgccaccac tacagcccct ccaccgcccc ctgctgcccc    1620
tcctgcggcc tcccaagcag cagcaacagc agccccaccg ccccaccag actatcacca    1680 tcaccaccag cagcacctgc tgaacagtag caataatggt ggcagtggtg ggataaacgg    1740
agagcagcag ccgcccgctt caaccccagg ggaccagagg aactcagccc tgattgcgct    1800
```

```
ccagggttcc ttgaaaagaa aacaggtagt taacctatct cctgccaaca gcaagcgacc    1860
caatggcttt gtggacaact catttcttga tatcaaaaga attcgtgttg gggagaatct    1920
ctctgcagga caaggtggcc tccaaataaa caatggacaa agtcagatta tgtcagggac    1980
cttgcctatg agccaagcac ccctgcgaaa gactaacact ctgccatccc atacacattc    2040
tcctggcaat ggcctgttta acatgggctt aaaggaggta agaaggagc  caggagagac    2100 tctgtcttgc agtaagcaca tggatggcca aatgacccaa gagaatattt ttcctaatag    2160
gtacggagac gaccctggag aacaactgat ggatcctgag ctgcaggaac tgttcaatga    2220
actgaccaac atatctgtgc ctcccatgag tgaccttgaa ctggagaaca tgatcaatgc    2280
caccataaag caggatgacc catttaacat tgacttgggt cagcaaagcc agaggagcac    2340
acctaggccc tccttaccca tggagaaaat agtgatcaaa agtgaatact caccgggctt    2400
gactcagggc ccctcaggct ctcctcagct gaggccccca tcagctggcc ccgcattctc    2460
catggccaac tctgccctct ccacttcgtc tccaatccct tcagtccctc agagccaggc    2520
tcagcctcag acaggctccg gagcaagccg ggccttgcca agctggcagg aagtatccca    2580
tgcccagcag ctcaaacaga tagctgctaa tcgtcagcag catgcccgga tgcagcagca    2640
ccagcagcag caccagccta ccaactggtc agccttgccc tcctctgctg gaccatcacc    2700
aggtccattt gggcaggaga aaatccccag cccttctttt ggtcagcaga cattcagccc    2760
acagagctcc cccatgcctg gggtagctgg cggcagcggc cagtcgaaag taatggctaa    2820
ctacatgtac aaggccggcc cctcagccca gggtgggcac ctagatgtcc tcatgcagca    2880
aaagcctcag gatctcagtc gaagttttat taacaacccg cacccagcca tggagccccg    2940
tcagggcaac accaagcctt tgtttcattt taactcagat caagcgaacc agcagatgcc    3000
ttctgttttg ccttcccaga caagccttc  tctcctacac tacacccaac agcaacagca    3060
gcaacagcag cagcagcagc agcagcagca gcagcaacag cagcagcagc agcaacagca    3120
acagcaacag caacagcaga gttcaatttc agctcaacaa cagcaacagc agcagagctc    3180
aatttcagcc caacagcagc agcagcagca acaacagcag cagcagcagc aacaacaaca    3240
gcaacaacag cagcagcagc agcagcaaca accatcttct cagcctgccc aatctctacc    3300
aagccagcct ttgctaaggt caccttgcc  acttcagcaa aagctcctac ttcagcaaat    3360
gcagaatcag cccattgcag gaatgggata ccaagtctcc caacaacaga gacaggatca    3420
acactctgtg gtaggccaga acacaggccc cagtccaagt cctaacccct gctcaaatcc    3480
aaacactgga agtggttaca tgaactccca gcaatcactg ttgaatcagc aattgatggg    3540
aaagaagcag actctacaga ggcagatcat ggagcagaaa cagcaacttc ttctccagca    3600
gcagatgctg gctgacgcgg agaaaattgc tccacaagat cagataaacc gacatttgtc    3660
aaggccacct ccagattata aagaccaaag aagaaatgtg gcaatatgc  aaccaactgc    3720 tcagtattct ggtggctcat ccacaataag cttaaactct aaccaggctt tggcaaaccc    3780
agtttcaaca cacaccattt taactcccaa ttccagcctc ctgtctactt ctcacgggac    3840
aagaatgcca tcattatcta cagcagttca gaatatgggg atgtatggaa atctgccttg    3900
taatcaacct aacacataca gtgtcacttc aggaatgaat caattgaccc aacagagaaa    3960
cccaaagcaa ttgttagcaa atcaaaacaa ccctatgatg ccacggccac ctaccttagg    4020
gccaagtaat aataacaatg tagccacttt tggagctgga tctgttggta attcacaaca    4080
attgagacca aatttaaccc catagtatgg caagcatgcca ccacagagaa catcaaacgt    4140
```

-continued

| | | | | |
|---|---|---|---|---|
| aatgatcaca | tccaacacaa | ctgcaccaaa | ctgggcctct | caagaaggaa caagcaaaca | 4200 |
| gcaagaagcc | ctgacgtctg | caggagtccg | cttcccaca | ggtacacctg cagcctatac | 4260 |
| cccaaatcag | tcactgcaac | aggcagtagg | tagccagcaa | ttttcccaga gggcagtggc | 4320 |
| tcctcctaac | cagttaacac | cagcagtgca | aatgagaccc | atgaaccaaa tgagccaaac | 4380 |
| actaaatggg | caaaccatgg | gtcccctcag | gggtctgaat | ctcagaccca atcagctaag | 4440 |
| cacacagatt | ttgcctaatt | tgaatcagtc | aggaacaggg | ttgaatcagt cgaggacggg | 4500 |
| catcaaccag | ccaccatccc | tgacgcccag | caattttcct | tcacccaacc aaagttccag | 4560 |
| ggcttttcaa | ggaactgacc | acagcagtga | cttagctttt | gacttcctca gccaacaaaa | 4620 |
| tgataacatg | ggccctgccc | taaacagtga | tgctgatttc | attgattctt tattgaagac | 4680 |
| agagcctggt | aatgatgact | ggatgaaaga | catcaatctt | gatgaaatct ggggaacaa | 4740 |
| ttcctaaaga | agaaagggaa | gacaatttac | aaactccaag | cactaaaagg cagtatatta | 4800 |
| cagaaactct | gtagaggctg | aactgttgat | gttcaggtgg | actacatgaa gataacatgc | 4860 |
| ttaaaaatgg | aaagcagaaa | gtaactgcag | tgatgaacat | tttggtccaa attcttgttt | 4920 |
| taaatcttac | acctgaaagt | aaaatattgg | gatcactttt | ccctgtctaa actccaggat | 4980 |
| acagtatcca | atttatccaa | acagaactgt | ggtgtcaatg | tgtaattaat tgtgtaaaat | 5040 |
| agccttccca | agtttctttt | tccctggaaa | ataaaaaagg | taatagaact tgtagtttat | 5100 |
| ttaaacccca | tgtcatgagg | aggtactagt | tccaagcaac | aaactcctta atttgctcta | 5160 |
| atagataggt | atggtttaat | ctttccattg | tgtcttttca | tttaattttc ctgaagcttg | 5220 |
| caggatagat | tgaaatgtta | taggtttgtt | tggagtaacc | aaacagtatg caaattaaga | 5280 |
| aaaagccaga | gaacctagaa | aacatccagt | ggattacaga | atttcttccc catattcact | 5340 |
| cctcactttt | acaattttcc | cacaatcctc | tacttcagtg | ggatgctgtg tctagtgatt | 5400 |
| aaacaaaaat | atagagctg | | | | 5419 |

<210> SEQ ID NO 4
<211> LENGTH: 2342
<212> TYPE: DNA
<213> ORGANISM: Homo sapiens

<400> SEQUENCE: 4

| | | | | |
|---|---|---|---|---|
| ccagccggcg | cttgcgcggt | ggcacgggcg | agtgggggg | cgaggaggtg gaggaggagg | 60 |
| aggaggagga | ggaggtggcg | gcgagaagat | ggcgacttcg | aacaatccgc ggaaattcag | 120 |
| cgagaagatc | gcgctgcaca | atcagaagca | ggcggaggag | acggcggcct tcgaggaggt | 180 |
| catgaaggac | ctgagcctga | cgcgggccgc | gcggctccag | ctccagaaat cccagtacct | 240 |
| gcaactgggc | cccagccgag | gccagtacta | tgcgggtcc | ctgcccaacg tgaaccagat | 300 |
| cgggagtggc | accatggacc | tgcccttcca | gacccctcc | caatcctcgg gcctggacac | 360 |
| cagccggacc | acccggcacc | atgggctggt | ggacagggtg | taccgggagc gtggccggct | 420 |
| cggctccca | caccgccggc | ccctgtcagt | ggacaaacac | ggacggcagg ccgacagctg | 480 |
| cccctatggc | accatgtacc | tctcaccacc | cgcggacacc | agctggagaa ggaccaattc | 540 |
| tgactccgcc | ctgcaccaga | gcacaatgac | gcccacgcag | ccagaatcct ttagcagtgg | 600 |
| gtcccaggac | gtgcaccaga | aaagagtctt | actgttaaca | gtcccaggaa tggaagagac | 660 |
| cacatcagag | gcagacaaaa | acctttccaa | gcaagcatgg | gacaccaaga agacgggtc | 720 |
| caggcccaag | tcctgtgagg | tccccggaat | caacatcttc | ccgtctgccg accaggaaaa | 780 |
| cactacagcc | ctgatccccg | ccacccacaa | cacaggggg | tccctgcccg acctgaccaa | 840 |

```
catccacttc ccctccccgc tcccgacccc gctggacccc gaggagccca ccttccctgc    900
actgagcagc tccagcagca ccggcaacct cgcggccaac ctgacgcacc tgggcatcgg    960
tggcgccggc cagggaatga gcacacctgg ctcctctcca cagcaccgcc cagctggcgt   1020
cagcccctg tccctgagca cagaggcaag gcgtcagcag gcatcgccca ccctgtcccc   1080
gctgtcaccc atcactcagg ctgtagccat ggacgccctg tctctggagc agcagctgcc   1140
ctacgccttc ttcacccagg cgggctccca gcagccaccg ccgcagcccc agccccgcc   1200
gcctcctcca cccgcgtccc agcagccacc accccgtca cccccacagg cgcccgtccg   1260
cctgcccct ggtggccccc tgttgcccag cgccagcctg actcgtgggc cacagccgcc   1320
cccgcttgca gtcacggtac cgtcctctct ccccagtcc cccccagaga acctggcca   1380
gccatcgatg gggatcgaca tcgcctcggc gccggctctg cagcagtacc gcactagcgc   1440
cggctccccg gccaaccagt ctcccacctc gccagtctcc aatcaaggct tctccccagg   1500
gagctccccg caactggagc agttcaacat gatggagaac gccatcagct ccagcagcct   1560
gtacagcccg ggctccacac tcaactactc gcaggcggcc atgatgggcc tcacgggcag   1620
ccacgggagc ctgccggact cgcagcaact gggatacgcc agccacggtg gcatcccaa   1680
catcatcctc acagtgacag agagtcccc cccagcctc tctaaagaac tgaccagcca   1740
ccgaggacac cttccggatg gaccgcctgt gagcgggcac gccggcaccc tgccgctcag   1800
ccgtcccgac ggcgcctccc cagcccgggg acggccgtgc tccgtccctc gccaacggcc   1860
gagcttgtga ttctgagctt gcaatgccgc caagcgcccc ccgccagccc gccccgggtt   1920
gtccacctcc cgcgaagccc aatcgcgagg ccgcgagccg ggccgtccac ccacccgccc   1980
gcccagggct gggctgggat cggaggccgt gagcctcccg cccctgcaga ccctccctgc   2040
actggctccc tcgcccccag ccccggggcc tgagccgtcc cctgtaagat gcgggaagtg   2100
tcagctcccg gcgtggcggg caggctcagg ggaggggcgc gcatggtccg ccagggctgt   2160
gggccgtggc gcatttttccg actgtttgtc cagctctcac tgccttcctt ggttcccggt   2220
cccccagccc atccgccatc cccagcccgt ggtcaggtag agagtgagcc ccacgccgcc   2280
ccagggagga ggcgccagag cgcggggcag acgcaaagtg aaataaacac tattttgacg   2340
gc                                                                 2342
```

<210> SEQ ID NO 5
<211> LENGTH: 31
<212> TYPE: PRT
<213> ORGANISM: Homo sapiens

<400> SEQUENCE: 5

Tyr Glu Arg Gly Arg Ala Glu Ser Ser Asp Arg Glu Arg Glu Ser Thr
1               5                   10                  15

Leu Gln Leu Leu Ser Leu Val Gln His Gly Gln Gly Ala Arg Lys
            20                  25                  30

<210> SEQ ID NO 6
<211> LENGTH: 31
<212> TYPE: PRT
<213> ORGANISM: Homo sapiens

<400> SEQUENCE: 6

Tyr Glu Ala Val Ser Pro Glu Arg Leu Glu Leu Glu Arg Gln His Thr
1               5                   10                  15

Phe Ala Leu His Gln Arg Cys Ile Gln Ala Lys Ala Lys Arg Ala

-continued

```
               20                  25                  30
```

<210> SEQ ID NO 7
<211> LENGTH: 31
<212> TYPE: PRT
<213> ORGANISM: Homo sapiens

<400> SEQUENCE: 7

```
Tyr Gln Gln Ala Gln Val Glu Gln Leu Glu Leu Glu Arg Arg Asp Thr
1               5                   10                  15

Val Ser Leu Tyr Gln Arg Thr Leu Glu Gln Arg Ala Lys Lys Ser
                20                  25                  30
```

<210> SEQ ID NO 8
<211> LENGTH: 31
<212> TYPE: PRT
<213> ORGANISM: Drosophila melanogaster

<400> SEQUENCE: 8

```
Tyr Glu Gln Ala Phe Asn Thr Val Cys Glu Gln Gln Asn Gln Glu Thr
1               5                   10                  15

Thr Val Leu Gln Lys Arg Phe Leu Glu Ser Lys Asn Lys Arg Ala
                20                  25                  30
```

<210> SEQ ID NO 9
<211> LENGTH: 31
<212> TYPE: PRT
<213> ORGANISM: Caenorhabditis elegans

<400> SEQUENCE: 9

```
Tyr Glu Lys Ala Arg Pro Glu Met Ile Ala Asn Gln Arg Ala Val Thr
1               5                   10                  15

Ala His Leu Phe Asn Arg Tyr Thr Glu Asp Glu Glu Arg Lys Arg
                20                  25                  30
```

<210> SEQ ID NO 10
<211> LENGTH: 23
<212> TYPE: DNA
<213> ORGANISM: Artificial
<220> FEATURE:
<223> OTHER INFORMATION: Synthetic

<400> SEQUENCE: 10
cgagaagatg gcgacttcga aca                                           23

<210> SEQ ID NO 11
<211> LENGTH: 28
<212> TYPE: DNA
<213> ORGANISM: Artificial
<220> FEATURE:
<223> OTHER INFORMATION: Synthetic

<400> SEQUENCE: 11
ccattgggtc gcttgctgtt ggcaggag                                      28

<210> SEQ ID NO 12
<211> LENGTH: 1024
<212> TYPE: PRT
<213> ORGANISM: Homo sapiens

<400> SEQUENCE: 12

```
Met Ala Thr Ser Asn Asn Pro Arg Lys Phe Ser Glu Lys Ile Ala Leu
1               5                   10                  15
```

-continued

His Asn Gln Lys Gln Ala Glu Thr Ala Ala Phe Glu Glu Val Met
         20                  25                  30

Lys Asp Leu Ser Leu Thr Arg Ala Ala Arg Leu Gln Gly Ser Leu Lys
         35                  40                  45

Arg Lys Gln Val Val Asn Leu Ser Pro Ala Asn Ser Lys Arg Pro Asn
50                   55                  60

Gly Phe Val Asp Asn Ser Phe Leu Asp Ile Lys Arg Ile Arg Val Gly
65                   70                  75                  80

Glu Asn Leu Ser Ala Gly Gln Gly Leu Gln Ile Asn Asn Gly Gln
                 85                  90                  95

Ser Gln Ile Met Ser Gly Thr Leu Pro Met Ser Gln Ala Pro Leu Arg
             100                 105                 110

Lys Thr Asn Thr Leu Pro Ser His Thr His Ser Pro Gly Asn Gly Leu
             115                 120                 125

Phe Asn Met Gly Leu Lys Glu Val Lys Lys Glu Pro Gly Glu Thr Leu
130                 135                 140

Ser Cys Ser Lys His Met Asp Gly Gln Met Thr Gln Glu Asn Ile Phe
145                 150                 155                 160

Pro Asn Arg Tyr Gly Asp Asp Pro Gly Glu Gln Leu Met Asp Pro Glu
                165                 170                 175

Leu Gln Glu Leu Phe Asn Glu Leu Thr Asn Ile Ser Val Pro Pro Met
             180                 185                 190

Ser Asp Leu Glu Leu Glu Asn Met Ile Asn Ala Thr Ile Lys Gln Asp
             195                 200                 205

Asp Pro Phe Asn Ile Asp Leu Gly Gln Gln Ser Gln Arg Ser Thr Pro
210                 215                 220

Arg Pro Ser Leu Pro Met Glu Lys Ile Val Ile Lys Ser Glu Tyr Ser
225                 230                 235                 240

Pro Gly Leu Thr Gln Gly Pro Ser Gly Ser Pro Gln Leu Arg Pro Pro
                245                 250                 255

Ser Ala Gly Pro Ala Phe Ser Met Ala Asn Ser Ala Leu Ser Thr Ser
             260                 265                 270

Ser Pro Ile Pro Ser Val Pro Gln Ser Gln Ala Gln Pro Gln Thr Gly
             275                 280                 285

Ser Gly Ala Ser Arg Ala Leu Pro Ser Trp Gln Glu Val Ser His Ala
             290                 295                 300

Gln Gln Leu Lys Gln Ile Ala Ala Asn Arg Gln Gln His Ala Arg Met
305                 310                 315                 320

Gln Gln His Gln Gln Gln His Gln Pro Thr Asn Trp Ser Ala Leu Pro
                325                 330                 335

Ser Ser Ala Gly Pro Ser Pro Gly Pro Phe Gly Gln Glu Lys Ile Pro
             340                 345                 350

Ser Pro Ser Phe Gly Gln Gln Thr Phe Ser Pro Gln Ser Ser Pro Met
             355                 360                 365

Pro Gly Val Ala Gly Gly Ser Gly Gln Ser Lys Val Met Ala Asn Tyr
370                 375                 380

Met Tyr Lys Ala Gly Pro Ser Ala Gln Gly Gly His Leu Asp Val Leu
385                 390                 395                 400

Met Gln Gln Lys Pro Gln Asp Leu Ser Arg Ser Phe Ile Asn Asn Pro
                405                 410                 415

His Pro Ala Met Glu Pro Arg Gln Gly Asn Thr Lys Pro Leu Phe His
             420                 425                 430

Phe Asn Ser Asp Gln Ala Asn Gln Gln Met Pro Ser Val Leu Pro Ser

-continued

```
                435                 440                 445
Gln Asn Lys Pro Ser Leu Leu His Tyr Thr Gln Gln Gln Gln Gln
            450                 455                 460
Gln Gln Gln Gln Gln Gln Gln Gln Gln Gln Gln Gln Gln Gln Gln
465                 470                 475                 480
Gln Gln Gln Gln Gln Gln Gln Gln Ser Ser Ile Ser Ala Gln Gln
                485                 490                 495
Gln Gln Gln Gln Gln Ser Ser Ile Ser Ala Gln Gln Gln Gln Gln
                500                 505                 510
Gln Gln Gln Gln Gln Gln Gln Gln Gln Gln Gln Gln Gln Gln Gln
            515                 520                 525
Gln Gln Gln Gln Gln Pro Ser Ser Gln Pro Ala Gln Ser Leu Pro Ser
530                 535                 540
Gln Pro Leu Leu Arg Ser Pro Leu Pro Leu Gln Gln Lys Leu Leu Leu
545                 550                 555                 560
Gln Gln Met Gln Asn Gln Pro Ile Ala Gly Met Gly Tyr Gln Val Ser
                565                 570                 575
Gln Gln Gln Arg Gln Asp Gln His Ser Val Val Gly Gln Asn Thr Gly
            580                 585                 590
Pro Ser Pro Ser Pro Asn Pro Cys Ser Asn Pro Asn Thr Gly Ser Gly
                595                 600                 605
Tyr Met Asn Ser Gln Gln Ser Leu Leu Asn Gln Gln Leu Met Gly Lys
            610                 615                 620
Lys Gln Thr Leu Gln Arg Gln Ile Met Glu Gln Lys Gln Gln Leu Leu
625                 630                 635                 640
Leu Gln Gln Gln Met Leu Ala Asp Ala Glu Lys Ile Ala Pro Gln Asp
                645                 650                 655
Gln Ile Asn Arg His Leu Ser Arg Pro Pro Asp Tyr Lys Asp Gln
                660                 665                 670
Arg Arg Asn Val Gly Asn Met Gln Pro Thr Ala Gln Tyr Ser Gly Gly
            675                 680                 685
Ser Ser Thr Ile Ser Leu Asn Ser Asn Gln Ala Leu Ala Asn Pro Val
            690                 695                 700
Ser Thr His Thr Ile Leu Thr Pro Asn Ser Ser Leu Leu Ser Thr Ser
705                 710                 715                 720
His Gly Thr Arg Met Pro Ser Leu Ser Thr Ala Val Gln Asn Met Gly
                725                 730                 735
Met Tyr Gly Asn Leu Pro Cys Asn Gln Pro Asn Thr Tyr Ser Val Thr
                740                 745                 750
Ser Gly Met Asn Gln Leu Thr Gln Gln Arg Asn Pro Lys Gln Leu Leu
            755                 760                 765
Ala Asn Gln Asn Asn Pro Met Met Pro Arg Pro Pro Thr Leu Gly Pro
            770                 775                 780
Ser Asn Asn Asn Asn Val Ala Thr Phe Gly Ala Gly Ser Val Gly Asn
785                 790                 795                 800
Ser Gln Gln Leu Arg Pro Asn Leu Thr His Ser Met Ala Ser Met Pro
                805                 810                 815
Pro Gln Arg Thr Ser Asn Val Met Ile Thr Ser Asn Thr Thr Ala Pro
                820                 825                 830
Asn Trp Ala Ser Gln Glu Gly Thr Ser Lys Gln Gln Glu Ala Leu Thr
            835                 840                 845
Ser Ala Gly Val Arg Phe Pro Thr Gly Thr Pro Ala Ala Tyr Thr Pro
850                 855                 860
```

```
Asn Gln Ser Leu Gln Gln Ala Val Gly Ser Gln Gln Phe Ser Gln Arg
865                 870                 875                 880

Ala Val Ala Pro Pro Asn Gln Leu Thr Pro Ala Val Gln Met Arg Pro
                885                 890                 895

Met Asn Gln Met Ser Gln Thr Leu Asn Gly Gln Thr Met Gly Pro Leu
                900                 905                 910

Arg Gly Leu Asn Leu Arg Pro Asn Gln Leu Ser Thr Gln Ile Leu Pro
            915                 920                 925

Asn Leu Asn Gln Ser Gly Thr Gly Leu Asn Gln Ser Arg Thr Gly Ile
        930                 935                 940

Asn Gln Pro Pro Ser Leu Thr Pro Ser Asn Phe Pro Ser Pro Asn Gln
945                 950                 955                 960

Ser Ser Arg Ala Phe Gln Gly Thr Asp His Ser Ser Asp Leu Ala Phe
                965                 970                 975

Asp Phe Leu Ser Gln Gln Asn Asp Asn Met Gly Pro Ala Leu Asn Ser
                980                 985                 990

Asp Ala Asp Phe Ile Asp Ser Leu  Leu Lys Thr Glu Pro Gly Asn Asp
            995                 1000                1005

Asp Trp  Met Lys Asp Ile Asn  Leu Asp Glu Ile Leu  Gly Asn Asn
    1010                1015                1020

Ser
```